United States Patent
Finlay et al.

(10) Patent No.: US 7,208,574 B1
(45) Date of Patent: Apr. 24, 2007

(54) HOST RECEPTOR FOR PATHOGENIC BACTERIA

(75) Inventors: B. Brett Finlay, Richmond (CA); Brendan Kenny, Redland (IE); Rebekah DeVinney, Calagary (CA); Markus Stein, Edmonton (CA)

(73) Assignee: The University of British Columbia, Vancouver, British Columbia ( * ) Notice: Subject to any disclaimer, the term of this patent is extended or adjusted under 35 U.S.C. 154(b) by 0 days.

(21) Appl. No.: 09/189,415

(22) Filed: Nov. 10, 1998

Related U.S. Application Data

(60) Provisional application No. 60/065,130, filed on Nov. 12, 1997.

(51) Int. Cl.
| | | |
|---|---|---|
| C07K 1/00 | (2006.01) | |
| C07K 2/00 | (2006.01) | |
| A61K 39/02 | (2006.01) | |
| A61K 39/108 | (2006.01) | |
| A61K 39/00 | (2006.01) | |
| A61K 38/00 | (2006.01) | |

(52) U.S. Cl. .............. 530/350; 530/300; 530/825; 424/234.1; 424/257.1; 424/190.1; 424/192.1; 424/242.1; 424/185.1; 514/2

(58) Field of Classification Search ............... 530/350, 530/825, 300; 424/234.1, 184.1, 185.1, 190.1, 424/241.1, 242.1, 257.1, 258.1, 192.1; 514/2
See application file for complete search history.

(56) References Cited

FOREIGN PATENT DOCUMENTS

| CA | 2 078 716 A | 3/1994 |
|---|---|---|
| WO | WO 97 40063 | 10/1997 |

OTHER PUBLICATIONS

McGuinnes et al. Lancet 337: 514-517, 1991.*
McGuinnes et al. 7: 505-514, 1993.*
Rudinger et al. In: Peptide Hormones. Parsons JA (Ed), University Park Press, 1976.*
Houghten et al. Vaccines86. Cold Spring Harbor Laboratory, pp. 21-25, 1986.*
Lazar et al. Mol. Cellular Biol. 8: 1247-1252, 1988.*
Webster et al. Mechanisms of Development 38: 25-32, 1992.*
Paton et al., "*Escherichia coli* translocated intimin receptor, putative chaperon protein, and intimin (eaeA) genes", Database EMBL—EMPRO Entry/Acc. No. AFO25311, Nov. 1, 1997.
Paton et al., "*Escherichi coli* strain 95SF2 translocation intimin receptor Tir (tir) gene, complete CDs; and unknown gene", Entry/Acc. No. AF070067, Jun. 24, 1998.
Paton et al., "Translocated intimin receiptors (Tir) of Shiga-toxigenic *Escherichia coli* isloates belonging to serogroups 026, 0111, and 0157 react with sera from patients with hemolytic-uremic syndrome and exhibit marked sequence heterogeneity," *Infection and Immunity*, vol. 66, No. 11, Nov. 1998, pp. 5580-5586.

Kenny et al., "Intimin-dependent binding of enteropathogenic *Escherichia coli* to host cells triggers novel signaling events, including tyrosine phosphyrylation of phospholipase C-gammal," *Infection and Immunity*, vol. 65, No. 7, Jul. 1997, pp. 2528-2536.
Kenny et al., "Enteropathogenic *E. coli* (EPEC) transfers its receptor for intimate adherence into mammailian cells," *Cell*, vol. 01, Nov. 14, 1997, pp. 511-520.
Deibel et al., "EspE, a novel secreted protein of attaching and affacing bacteria; is directly translocated into infected host cells, where it appears as a tyrosine-phosphorylated 90 kDa protein," *Molecular Microbiology*, vol. 28, No. 3, May, 1998, pp. 463-474.
Roshenshine et al., "Pathogenic bacterium triggers epithelial signals to form a functional bacterial receptor that mediates actin pseudopod formation," *The EMBO Journal*, vol. 15, No. 11, 1996, pp. 2613-2624.
Abe et al., Characterization of two virulence proteins secreted by rabbit enteropathogenic *Escherichia coli*, EspA and EspB, whose maximal expression is sensitive to host body temperature, *Infenction and Immunity*, 65(9):3547-3555.
Finlay et al., Enterpathogenic *E. coli* exploitation of host epithelial cells, *Animals of New York Academy of Sciences*, 797:26-31 (1996).
Jarvis et al., Enteropathogenic *Escherichia coli* contains a putative type III secretion system necessary for the exporof proteins involved in attaching and effacing lesion formation, *PNAS*, U.S.A. 92(17):7996-8000 (Aug. 15, 1995).
Jarvis et al., Secretion of extracellular proteins by enterhemorrhagic *Escherichia coli* via a putative type III secretion system, *Infection and Immunity*, 64:(11):4826-4829 (Nov. 11, 1996).
Kenny et al., EspA, a protein secreted by enteropathogenic *Escherichia coli* is required to induce signals in epithelial cells, Molecular Microbiology, 20(2);313-323 (1996).
Kenny et al., Protein secretion by enteropathogenic *Escherichia coli* is essential for tranducing signals to epithelial cells, *PNAS*, U.S.A. 92(17):7991-7995 (Aug. 15, 1995).

* cited by examiner

*Primary Examiner*—S. Devi
(74) *Attorney, Agent, or Firm*—Woodcock Washburn LLP

(57) ABSTRACT

A polypeptide, called Tir (for translocated intimin receptor, which is secreted by attaching and effacing pathogens, such as the enteropathogenic (EPEC) and enterohemorrhagic (EHEC) *E. coli*. These bacterial pathogens inserts their own receptors into mammalian cell surfaces, to which the bacterial pathogen then adheres to trigger additional host signaling events and actin nucleation. Diagnosis of disease caused by pathogenic *E. coli* can be performed by the use of antibodies which bind to Tir to detect the protein or the use of nucleic acid probes for detection of nucleic acids encoding Tir polypeptide. Isolated nucleic acid sequences encoding Tir polypeptide, Tir peptides, a recombinant method for producing recombinant Tir, antibodies which bind to Tir, and a kit for the detection of Tir-producing *E. coli* are provided. A method of immunizing a host with Tir to induce a protective immune response to Tir or a second polypeptide of interest is also provided. A method for screening for compounds which interfere with the binding of bacterial pathogens to their receptors is further provided.

8 Claims, 13 Drawing Sheets

```
cggctgcataccgttacgtcatagtaatataaaggaacgtgtcaaatttctaaataaaag        60
    tir →
gatatatgtATGCCTATTGGTAACCTTGGTAATAATGTAAATGGCAATCATTTAATTCCC       120
         M  P  I  G  N  L  G  N  N  V  N  G  N  H  L  I  P
CCTGCGCCGCCACTACCTTCACAAACAGACGGCGCGGCACGGGGAGGAACTGGTCATCTA       180
 P  A  P  P  L  P  S  Q  T  D  G  A  A  R  G  G  T  G  H  L
ATTAGCTCTACAGGAGCATTAGGATCTCGTTCATTGTTTTCTCCCCTGAGAAATTCTATG       240
 I  S  S  T  G  A  L  G  S  R  S  L  F  S  P  L  R  N  S  M
GCTGATTCTGTCGATTCCAGAGATATTCCAGGACTTCCTACAAACCCATCGAGGCTTGCT       300
 A  D  S  V  D  S  R  D  I  P  G  L  P  T  N  P  S  R  L  A
GCAGCTACATCTGAGACATGCTTGCTTGGAGGATTTGAAGTTCTCCATGATAAGGGGCCA       360
 A  A  T  S  E  T  C  L  L  G  G  F  E  V  L  H  D  K  G  P
CTTGATATTCTCAATACGCAAATTGGACCCTCTGCATTTCGTGTTGAAGTGCAGGCAGAT       420
 L  D  I  L  N  T  Q  I  G  P  S  A  F  R  V  E  V  Q  A  D
GGTACTCATGCCGCTATTGGAGAAAAAAATGGTTTGGAGGTTAGCGTTACATTAAGTCCT       480
 G  T  H  A  A  I  G  E  K  N  G  L  E  V  S  V  T  L  S  P
CAAGAATGGAGCAGCTTGCAATCTATTGATACTGAGGGTAAAAACAGATTTGTTTTTACC       540
 Q  E  W  S  S  L  Q  S  I  D  T  E  G  K  N  R  F  V  F  T
GGGGGACGTGGCGGTAGTGGGCATCCGATGGTCACTGTCGCATCAGATATCGCGGAAGCT       600
 G  G  R  G  G  S  G  H  P  M  V  T  V  A  S  D  I  A  E  A
CGTACGAAAATACTGGCCAAATTAGACCCAGACAATCATGGAGGACGTCAACCCAAGGAC       660
 R  T  K  I  L  A  K  L  D  P  D  N  H  G  G  R  Q  P  K  D
GTTGATACGCGTTCTGTTGGTGTTGGCAGCGCTTCGGGAATAGATGATGGCGTTGTTAGC       720
 V  D  T  R  S  V  G  V  G  S  A  S  G  I  D  D  G  V  V  S
GAAACCCATACTTCAACAACAAATTCCAGCGTTCGCTCAGATCCTAAAATTCTGGGTTTCT       780
 E  T  H  T  S  T  T  N  S  S  V  R  S  D  P  K  F  W  V  S
GTCGGCGCAATTGCTGCTGGTTTAGCGGGACTGGCGGCAACTGGTATTGCACAGGCGTTG       840
 V  G  A  I  A  A  G  L  A  G  L  A  A  T  G  I  A  Q  A  L
GCTTTGACACCGGAACCGGATGATCCTACAACCACCGATCCTGATCAGGCCGCAAATGCT       900
 A  L  T  P  E  P  D  D  P  T  T  T  D  P  D  Q  A  A  N  A
GCAGAAAGTGCAACAAAAGATCAGTTAACGCAAGAAGCATTCAAGAACCCTGAGAACCAG       960
 A  E  S  A  T  K  D  Q  L  T  Q  E  A  F  K  N  P  E  N  Q
AAAGTTAACATCGATGCGAACGGAAATGCTATTCCGTCTGGGGAATTAAAAGATGATATT      1020
 K  V  N  I  D  A  N  G  N  A  I  P  S  G  E  L  K  D  D  I
GTTGAGCAAATAGCACAACAAGCTAAAGAGGCTGGTGAGGTGGCCAGACAGCAGGCTGTT      1080
 V  E  Q  I  A  Q  Q  A  K  E  A  G  E  V  A  R  Q  Q  A  V
GAAAGCAATGCACAGGCGCAGCAGCGATATGAGGATCAGCATGCCAGACGTCAGGAGGAA      1140
 E  S  N  A  Q  A  Q  Q  R  Y  E  D  Q  H  A  R  R  Q  E  E
TTACAGCTTTCATCGGGTATTGGTTACGGCCTCAGCAGTGCATTGATTGTTGCTGGGGGA      1200
 L  Q  L  S  S  G  I  G  Y  G  L  S  S  A  L  I  V  A  G  G
```

*FIG. 6A*

```
ATTGGTGCTGGTGTAACGACTGCGCTCCATAGACGAAATCAGCCGGCAGAACAGACAACT  1260
 I  G  A  G  V  T  T  A  L  H  R  R  N  Q  P  A  E  Q  T  T
ACTACAACAACACATACGGTAGTGCAGCAACAGACCGGAGGGATACCCCAGCACAAGGTG  1320
 T  T  T  T  H  T  V  V  Q  Q  Q  T  G  G  I  P  Q  H  K  V
GCACTGATGCCACAAGAGCGAAGACGCTTCTCTGATAGACGTGATTCGCAGGGGAGTGTT  1380
 A  L  M  P  Q  E  R  R  R  F  S  D  R  R  D  S  Q  G  S  V
GCATCGACACACTGGTCAGATTCCTCTAGCGAAGTGGTTAATCCATATGCTGAAGTTGGG  1440
 A  S  T  H  W  S  D  S  S  S  E  V  V  N  P  Y  A  E  V  G
GGGGCTCGGAATAGTCTATCGGCTCATCAGCCAGAAGAGCATATTTATGATGAGGTCGCT  1500
 G  A  R  N  S  L  S  A  H  Q  P  E  E  H  I  Y  D  E  V  A
GCAGATCCTGGTTATAGCGTTATTCAGAATTTTTCAGGGAGCGGCCCAGTTACCGGAAGG  1560
 A  D  P  G  Y  S  V  I  Q  N  F  S  G  S  G  P  V  T  G  R
TTAATAGGAACTCCAGGGCAAGGTATCCAAAGTACTTATGCGCTTCTGGCAAACAGCGGC  1620
 L  I  G  T  P  G  Q  G  I  Q  S  T  Y  A  L  L  A  N  S  G
GGATTGCGTTTAGGTATGGGAGGATTAACGAGTGGTGGCGAGACGGCAGTAAGTTCTGTA  1680
 G  L  R  L  G  M  G  G  L  T  S  G  G  E  T  A  V  S  S  V
AATGCCGCACCAACGCCGGGACCAGTACGTTTCGTTTAAatatatctgtgagtatttagt  1740
 N  A  A  P  T  P  G  P  V  R  F  V  *
tgaggttggggtggggtgggggggcgtttactagcgttaatgtttcagagaacaacgtt  1800
                                                     orFU →
gcagcatgggtaactcttgaacttctgttattataatcaattaagagaaattataATGTC  1860
                                                          M  S
ATCAAGATCTGAACTTTTATTAGATAGGTTTGCGGAAAAAATTGGTGTTGGATCTATTTC  1920
 S  R  S  E  L  L  L  D  R  F  A  E  K  I  G  V  G  S  I  S
```

*FIG. 6B*

```
EPEC      1    MPIGNLGNNVNGNHLIPPAPPLPSQTDGAARGGIGHLISSTG
EHEC      1    MPIGNLGHNPNVNNSIPPAPPLPSQTDGAG..GRGQLINSTG
RDEC-1    1    .........................................

EPEC     43    ALGSRSLFSPLRNSMADSVDSRL.DIPGLPTNPSRLAAATSE
EHEC     41    PLGSRALFTPVRNSMADSGDNRASDVPGLPVNPMRLAAS..E
RDEC-1    1    ...........NSVADAADSRASDIPGLPTNPLRFAAS..E

EPEC     83    TCLLGGFEVLHDKGPLDILNTQIGPSAFRVEVQADGTHAAIG
EHEC     81    ITLNDGFEVLHDHGPLDTLNRQIGSSVFRVETQEDGKHIAVG
RDEC-1   29    VSLHGALEVLHDKGGLDTLNSAIGSSLFRVETRDDGSHVAIG

EPEC    125    EKNGLEVSVTLSPQEWSSLQSIDTEGKNRFVFTGGRGGSGHP
EHEC    123    QRNGVETSVVLSDQEYARLQSIDPEGKDKFVFTGGRGGAGHA
RDEC-1   71    QKNGLETTVVLSEQEFSSLQSLDPEGKNKFVFTGGRGGPGHA

EPEC    167    MVTVASDIAEARTKILAKLDPDNHGGROPKDVDTRSVGVGSA
EHEC    165    MVTVASDITEARQRILELLEPKGTG.ESKGAGESKGVGELRE
RDEC-1  113    MVTVASDIAEARQRIIDKLEPK.........DTKETKEPGD

EPEC    209    SGIDDGVVSETHTSTTNSSVRSDPKFWSVGAIAAGLAGLAA
EHEC    206    SNSGAENTTETQTSTSTSSLRSDPKLWLALGTVATGLIGLAA
RDEC-1  145    PNSGEGKIIEIHTSTSTSSLRADPKLWLSLGTIAAGLIGMAA

EPEC    251    TGIAQALALTPEPDDPTTTDPDQAANAAESATKDQLTQEAFK
EHEC    248    TGIVQALALTPEPDSPTTTDPDAAASATETATRDQLTKEAFQ
RDEC-1  187    TGIAQAVALTPEPDDPITTDPDAAANTAEAAAKDQLTKEAFQ

EPEC    293    NPENQKVNIDANGNAIPSGELKDDIVEQIAQQAKEAGEVARQ
EHEC    290    NPDNQKVNIDELGNAIPSGVLKDDVVANIEFQAKAAGEEAKQ
RDEC-1  229    NPDNQKVNIDENGNAIPSGELKDDVVAQIAEQAKAAGEQARQ

EPEC    335    QAVESNAQAQQRYEDQHARRQEELQLSSGIGYGLSSALIVAG
EHEC    332    QAIENNAQAQKKYDEQQAKRQEELKVSSGAGYGLSGALILGG
RDEC-1  271    EAIESNSQAQQKYDEQHAKREQEMSLSSGVGYGISGALILGG

EPEC    377    GIGAGVTIALHRRNQPAEQTTTTTT.......HTVQQQTGG
EHEC    374    GIGVAVTAALHRKNQPVEQTTTTTTTTTTTSARTVENKPANN
RDEC-1  313    GIGAGVTAALHRKNQPAEQTTTTRT........VVDNQPTNN
```

*FIG. 9A*

```
EPEC    412   IPQHKVALMPQERRRFSDRRDSQGSVASTHWSDSSS.EVVNP
EHEC    416   TPAQGNVDTPGSEDTMESRRSSMASTSSTFFDTSSIGTVQNP
RDEC-1  347   ASAQGNTDTSGPEESPASRRNSNASLASNGSDTSSTGTVENP
                                        473
EPEC    453   YAEVGGARNSLSAHQPEEHIYDEVAADPG...YSVIQNFS.G
EHEC    458   YADVKTSLHDSQVPTSNSNTSVQNMGNTDSVVYSTIQHPPRD
RDEC-1  389   YADVGMPRNDSLARISEEPIYDEVAADPN...YSVIQHFS.G

EPEC    491   SGPVTGRLIGTPGQGIQSTYALLANSGGLRLGMGGLTSGGET
EHEC    500   TTDNGARLLGNPSAGIQSTYARLALSGGLRHDMGGLTGGSNS
RDEC-1  427   NSPVTGRLVGTPGQGIQSTYALLASSGGLRLGMGGLTGGGES

EPEC    533   AVSSVNAAPTPGPVRFV
EHEC    542   AVNTSNNPPAPGSHRFV
RDEC-1  469   AVSTANAAPTPGPARFV
```

FIG. 9B

```
                              SEQUENCE LISTING

<160> NUMBER OF SEQ ID NOS: 14

<210> SEQ ID NO 1
<211> LENGTH: 1920
<212> TYPE: DNA
<213> ORGANISM: Escherichia coli

<400> SEQUENCE: 1
cggctgcata ccattacgtc atagtaatat aaaggaacgt gtcaaatttc taaataaaag      60
gatatatgta tgcctattgg taaccttggt aataatgtaa atggcaatca tttaattccc     120
cctgcgccgc cactaccttc acaaacagac ggcgcggcac ggggaggaac tggtcatcta     180
attagctcta caggagcatt aggatctcgt tcattgtttt ctcccctgag aaattctatg     240
gctgattctg tcgattccag agatattcca ggacttccta caaacccatc gaggcttgct     300
gcagctacat ctgagacatg cttgcttgga ggatttgaag ttctccatga taaggggcca     360
cttgatattc tcaatacgca aattggaccc tctgcatttc gtgttgaagt gcaggcagat     420
ggtactcatg ccgctattgg agaaaaaaat ggtttggagg ttagcgttac attaagtcct     480
caagaatgga gcagcttgca atctattgat actgagggta aaaacagatt tgtttttacc     540
gggggacgtg gcggtagtgg gcatccgatg gtcactgtcg catcagatat cgcggaagct     600
cgtacgaaaa tactggccaa attagaccca gacaatcatg gaggacgtca acccaaggac     660
gttgatacgc gttctgttgg tgttggcagc gcttcgggaa tagatgatgg cgttgttagc     720
gaaacccata cttcaacaac aaattccagc gttcgctcag atcctaaatt ctgggtttct     780
gtcggcgcaa ttgctgctgg tttagcggga ctggcggcaa ctggtattgc acaggcgttg     840
gctttgacac cggaaccgga tgatcctaca accaccgatc ctgatcaggc cgcaaatgct     900
gcagaaagtg caacaaaaga tcagttaacg caagaagcat tcaagaaccc tgagaaccag     960
```

-continued

```
aaagttaaca tcgatgcgaa cggaaatgct attccgtctg gggaattaaa agatgatatt    1020
gttgagcaaa tagcacaaca agctaaagag gctggtgagg tggccagaca gcaggctgtt    1080
gaaagcaatg cacaggcgca gcagcgatat gaggatcagc atgccagacg tcaggaggaa    1140
ttacagcttt catcgggtat tggttacggc ctcagcagtg cattgattgt tgctggggga    1200
attggtgctg gtgtaacgac tgcgctccat agacgaaatc agccggcaga acagacaact    1260
actacaacaa cacatacggt agtgcagcaa cagaccggag gataccccca gcacaaggtg    1320
gcactgatgc cacaagagcg aagacgcttc tctgatagac gtgattcgca ggggagtgtt    1380
gcatcgacac actggtcaga ttcctctagc gaagtggtta atccatatgc tgaagttggg    1440
ggggctcgga atagtctatc ggctcatcag ccagaagagc atatttatga tgaggtcgct    1500
gcagatcctg gttatagcgt tattcagaat ttttcaggga gcggcccagt taccggaagg    1560
ttaataggaa ctccagggca aggtatccaa agtacttatg cgcttctggc aaacagcggc    1620
ggattgcgtt taggtatggg aggattaacg agtggtggcg agacggcagt aagttctgta    1680
aatgccgcac caacgcaggg accagtacgt ttcgtttaaa tatatctgtg agtatttagt    1740
tgaggttggg gtggggtggg gggcgttttt actagcgtta atgtttcaga gaacaacgtt    1800
gcagcatggg taactcttga acttctgtta ttataatcaa ttaagagaaa ttataatgtc    1860
atcaagatat gaactttat tagataggtt tgcggaaaaa attggtgttg gatctatttc    1920
```

<210> SEQ ID NO 2

<400> SEQUENCE: 2

000

<210> SEQ ID NO 3
<211> LENGTH: 1723
<212> TYPE: DNA
<213> ORGANISM: Escherichia coli

<400> SEQUENCE: 3

```
atgcctattg gtaaccttgg tcataatccc aatgtgaata attcaattcc tcctgcacct      60
ccattacctt cacaaaccga cggtgcaggg gggcgtggtc agctcattaa ctctacgggg     120
ccgttgggat ctcgtgcgct atttacgcct gtaaggaatt ctatggctga ttctggcgac     180
aatcgtgcca gtgatgttcc tggacttcct gtaaatccga tgcgcctggc ggcgtctgag     240
ataacactga tgatggatt tgaagttctt catgatcatg gtccgctcga tactcttaac     300
aggcagattg gctcttcggt atttcgagtt gaaactcagg aagatggtaa acatattgct     360
gtcggtcaga ggaatggtgt tgagacctct gttgtttta gtgatcaaga gtacgctcgc     420
ttgcagtcca ttgatcctga aggtaaagac aaatttgtat ttactggagg ccgtggtggt     480
gctgggcatg ctatggtcac cgttgcttca gatatcacgg aagcccgcca aggatactg     540 gagctgttag agcccaaagg gaccggggag tccaaggtg ctggggagtc aaaaggcgtt     600
ggggagttga gggagtcaaa tagcggtgcg gaaaacacca cagaaactca gacctcaacc     660
tcaacttcca gccttcgttc agatcctaaa ctttggttgg cgttgggac tgttgctaca     720 ggtctgatag ggtggcggc gacgggtatt gtacaggcgc ttgcattgac gccggagccg     780
gatagcccaa ccacgaccga ccctgatgca gctgcaagtg caactgaaac tgcgacaaga     840
gatcagttaa cgaaagaagc gttccagaac ccagataatc aaaaagttaa tatcgatgag     900
ctcggaaatg cgattccgtc aggggtattg aaagatgatg ttgttgcgaa tatagaagag     960
```

-continued

| | |
|---|---|
| caggctaaag cagcaggcga agaggccaaa cagcaagcca ttgaaaataa tgctcaggcg | 1020 |
| caaaaaaat atgatgaaca acaagctaaa cgccaggagg agctgaaagt ttcatcgggg | 1080 |
| gctggctacg gtcttagtgg cgcattgatt cttggtgggg gaattggtgt tgccgtcacc | 1140 |
| gctgcgcttc atcgaaaaaa tcagccggta gaacaaacaa caacaactac tactacaact | 1200 |
| acaactacaa gcgcacgtac ggtagagaat aagcctgcaa ataatacacc tgcacagggc | 1260 |
| aatgtagata ccctgggtc agaagatacc atggagagca gacgtagctc gatggctagc | 1320 |
| acctcgtcga ctttctttga cacttccagc ataggaccg tgcagaatcc gtatgctgat | 1380 |
| gttaaaacat cgctgcatga ttcgcaggtg ccgacttcta attctaatac gtctgttcag | 1440 |
| aatatgggga atacagattc tgttgtatat agcaccattc aacatcctcc ccgggatact | 1500 |
| actgataacg gcgcacggtt attaggaaat ccaagtgcgg ggattcaaag cacttatgcg | 1560 |
| cgtctggcgc taagtggtgg attacgccat gacatgggag gattaacggg ggggagtaat | 1620 |
| agcgctgtga atacttcgaa taacccacca gcgccgggat ccatcgtttt cgtctaaata | 1680 |
| tatccataat cattttattt agagggaggg agggggggaag tct | 1723 |

<210> SEQ ID NO 4

<400> SEQUENCE: 4

000

<210> SEQ ID NO 5
<211> LENGTH: 1460
<212> TYPE: DNA
<213> ORGANISM: Escherichia coli

<400> SEQUENCE: 5

| | |
|---|---|
| aattctgttg ctgatgctgc tgattctcgt gccagtgata ttcccggact tcctacaaat | 60 |
| ccactgcgct ttgctgcgtc cgaggtatct ttgcatggtg cgcttgaagt tcttcatgat | 120 |
| aaagggggc ttgatactct taactctgct attggatctt cgttattccg tgttgaaact | 180 |
| cgggatgatg gcagccatgt tgctatcggg caaaaaaatg gcctcgagac cactgttgtt | 240 |
| ttaagtgagc aagagttttc tagcttacag tcccttgatc ctgaaggtaa aaacaaattt | 300 |
| gtatttactg gaggccgcgg tggcccaggg catgctatgg tcacggttgc ttcagatatc | 360 |
| gccgaagccc gtcagaggat aatagataaa ttagaaccaa aggatacaaa ggagacgaag | 420 |
| gagccagggg atccaaatag tggcgaggga aaaatcattg aaattcatac ctcaacctca | 480 |
| acttctagcc tccgtgcaga tcctaaactt tggttgtcat tggggactat tgctgcaggt | 540 |
| ctgataggga tggctgcgac ggggattgca caggctgttg cgttgactcc agagccggat | 600 |
| gacccaatca ctaccgaccc tgatgctgca gcaaacacag ctgaagcagc ggcaaaagat | 660 |
| cagttaacga agaagcatt ccagaaccca gataaccaga agttaatat cgatgagaac | 720 |
| ggaaatgcaa ttccgtccgg ggaactaaaa gatgatgttg ttgcgcaaat agcagaacaa | 780 |
| gctaaagcgg cgggtgaaca ggccagacag gaagctattg aaagtaattc tcaggcgcag | 840 |
| caaaaatatg atgaacagca tgctaaacgc gaacaggaaa tgtctctttc atcggggtt | 900 |
| ggctacggta ttagtggtgc gctgattctt ggcgggggaa ttggtgccgg tgttactgct | 960 |
| gctcttcatc ggaaaaacca accggcagaa caaacaatca ctacacgtac ggtagtcgat | 1020 |
| aatcagccta cgaataacgc atctgcgcag ggcaatactg acacaagtgg gccagaagag | 1080 |
| tccccggcga gcagacgtaa ttcgaatgcc agcctcgcat cgaacgggtc tgacacctcc | 1140 |

-continued

```
agcacgggca cggtagagaa tccgtatgct gacgttggaa tgcccagaaa tgattcactg    1200
gctcgcattt cagaggaacc tatttatgat gaggtcgctg cagatcctaa ttatagcgtc    1260
attcaacatt tttcaggaaa cagcccagtt accggaaggt tagtgggaac cccagggcaa    1320
ggtatccaaa gtacttatgc gcttctggca agcagcggcg gattgcgttt aggtatggga    1380
ggattaacgg ggggtggcga gagcgcagta agtactgcca atgccgcacc aacgccggga    1440
cccgcacgtt tcgtttaaat                                                1460
```

<210> SEQ ID NO 6

<400> SEQUENCE: 6

000

<210> SEQ ID NO 7
<211> LENGTH: 30
<212> TYPE: PRT
<213> ORGANISM: Escherichia coli

<400> SEQUENCE: 7

Pro Ile Gly Asn Leu Gly Asn Asn Val Asn Gly Asn His Leu Ile Pro
1               5                   10                  15

Pro Ala Pro Pro Leu Pro Ser Gln Thr Asp Gly Ala Ala Arg
            20                  25                  30

<210> SEQ ID NO 8
<211> LENGTH: 26
<212> TYPE: DNA
<213> ORGANISM: Artificial
<220> FEATURE:
<223> OTHER INFORMATION: Primer

<400> SEQUENCE: 8
aaagtcgaca agaacctgag aaccag                                         26

<210> SEQ ID NO 9
<211> LENGTH: 30
<212> TYPE: DNA
<213> ORGANISM: Artificial
<220> FEATURE:
<223> OTHER INFORMATION: Primer

<400> SEQUENCE: 9
tttgtcgact tatgtttgtg aaggtagtgg                                     30

<210> SEQ ID NO 10
<211> LENGTH: 549
<212> TYPE: PRT
<213> ORGANISM: Escherichia coli

<400> SEQUENCE: 10

Met Pro Ile Gly Asn Leu Gly Asn Asn Val Asn Gly Asn His Leu Ile
1               5                   10                  15

Pro Pro Ala Pro Pro Leu Pro Ser Gln Thr Asp Gly Ala Ala Arg Gly
            20                  25                  30

Gly Thr Gly His Leu Ile Ser Ser Thr Gly Ala Leu Gly Ser Arg Ser
        35                  40                  45

Leu Phe Ser Pro Leu Arg Asn Ser Met Ala Asp Ser Val Asp Ser Arg
    50                  55                  60

Asp Ile Pro Gly Leu Pro Thr Asn Pro Ser Arg Leu Ala Ala Ala Thr
65                  70                  75                  80

-continued

```
Ser Glu Thr Cys Leu Leu Gly Gly Phe Glu Val Leu His Asp Lys Gly
                 85                  90                  95
Pro Leu Asp Ile Leu Asn Thr Gln Ile Gly Pro Ser Ala Phe Arg Val
            100                 105                 110
Glu Val Gln Ala Asp Gly Thr His Ala Ala Ile Gly Glu Lys Asn Gly
            115                 120                 125
Leu Glu Val Ser Val Thr Leu Ser Pro Gln Glu Trp Ser Ser Leu Gln
    130                 135                 140
Ser Ile Asp Thr Glu Gly Lys Asn Arg Phe Val Phe Thr Gly Gly Arg
145                 150                 155                 160
Gly Gly Ser Gly His Pro Met Val Thr Val Ala Ser Asp Ile Ala Glu
                165                 170                 175
Ala Arg Thr Lys Ile Leu Ala Lys Leu Asp Pro Asp Asn His Gly Gly
            180                 185                 190
Arg Gln Pro Lys Asp Val Asp Thr Arg Ser Val Gly Val Gly Ser Ala
        195                 200                 205
Ser Gly Ile Asp Asp Gly Val Val Ser Glu Thr His Thr Ser Thr Thr
    210                 215                 220
Asn Ser Ser Val Arg Ser Asp Pro Lys Phe Trp Val Ser Val Gly Ala
225                 230                 235                 240
Ile Ala Ala Gly Leu Ala Gly Leu Ala Ala Thr Gly Ile Ala Gln Ala
                245                 250                 255
Leu Ala Leu Thr Pro Glu Pro Asp Asp Pro Thr Thr Thr Asp Pro Asp
            260                 265                 270
Gln Ala Ala Asn Ala Ala Glu Ser Ala Thr Lys Asp Gln Leu Thr Gln
        275                 280                 285
Glu Ala Phe Lys Asn Pro Glu Asn Gln Lys Val Asn Ile Asp Ala Asn
    290                 295                 300
Gly Asn Ala Ile Pro Ser Gly Glu Leu Lys Asp Asp Ile Val Glu Gln
305                 310                 315                 320
Ile Ala Gln Gln Ala Lys Glu Ala Gly Glu Val Ala Arg Gln Gln Ala
                325                 330                 335
Val Glu Ser Asn Ala Gln Ala Gln Gln Arg Tyr Glu Asp Gln His Ala
            340                 345                 350
Arg Arg Gln Glu Glu Leu Gln Leu Ser Ser Gly Ile Gly Tyr Gly Leu
        355                 360                 365
Ser Ser Ala Leu Ile Val Ala Gly Gly Ile Gly Ala Gly Val Thr Thr
    370                 375                 380
Ala Leu His Arg Arg Asn Gln Pro Ala Glu Gln Thr Thr Thr Thr Thr
385                 390                 395                 400
Thr His Thr Val Val Gln Gln Thr Gly Ile Pro Gln His Lys
                405                 410                 415
Val Ala Leu Met Pro Gln Glu Arg Arg Phe Ser Asp Arg Asp
            420                 425                 430
Ser Gln Gly Ser Val Ala Ser Thr His Trp Ser Asp Ser Ser Glu
        435                 440                 445
Val Val Asn Pro Tyr Ala Glu Val Gly Gly Ala Arg Asn Ser Leu Ser
    450                 455                 460
Ala His Gln Pro Glu His Ile Tyr Asp Glu Val Ala Ala Asp Pro
465                 470                 475                 480
Gly Tyr Ser Val Ile Gln Asn Phe Ser Gly Ser Gly Pro Val Thr Gly
                485                 490                 495
```

```
Arg Leu Ile Gly Thr Pro Gly Gln Gly Ile Gln Ser Thr Tyr Ala Leu
            500                 505                 510

Leu Ala Asn Ser Gly Gly Leu Arg Leu Gly Met Gly Gly Leu Thr Ser
        515                 520                 525

Gly Gly Glu Thr Ala Val Ser Ser Val Asn Ala Ala Pro Thr Gln Gly
530                 535                 540

Pro Val Arg Phe Val
545

<210> SEQ ID NO 11
<211> LENGTH: 558
<212> TYPE: PRT
<213> ORGANISM: Escherichia coli

<400> SEQUENCE: 11

Met Pro Ile Gly Asn Leu Gly His Asn Pro Asn Val Asn Asn Ser Ile
1               5                   10                  15

Pro Pro Ala Pro Pro Leu Pro Ser Gln Thr Asp Gly Ala Gly Gly Arg
            20                  25                  30

Gly Gln Leu Ile Asn Ser Thr Gly Pro Leu Gly Ser Arg Ala Leu Phe
        35                  40                  45

Thr Pro Val Arg Asn Ser Met Ala Asp Ser Gly Asp Asn Arg Ala Ser
    50                  55                  60

Asp Val Pro Gly Leu Pro Val Asn Pro Met Arg Leu Ala Ala Ser Glu
65                  70                  75                  80

Ile Thr Leu Asn Asp Gly Phe Glu Val Leu His Asp His Gly Pro Leu
                85                  90                  95

Asp Thr Leu Asn Arg Gln Ile Gly Ser Ser Val Phe Arg Val Glu Thr
            100                 105                 110

Gln Glu Asp Gly Lys His Ile Ala Val Gly Gln Arg Asn Gly Val Glu
        115                 120                 125

Thr Ser Val Val Leu Ser Asp Gln Glu Tyr Ala Arg Leu Gln Ser Ile
    130                 135                 140

Asp Pro Glu Gly Lys Asp Lys Phe Val Phe Thr Gly Arg Gly Arg Gly
145                 150                 155                 160

Ala Gly His Ala Met Val Thr Val Ala Ser Asp Ile Thr Glu Ala Arg
                165                 170                 175

Gln Arg Ile Leu Glu Leu Leu Glu Pro Lys Gly Thr Gly Glu Ser Lys
            180                 185                 190

Gly Ala Gly Glu Ser Lys Gly Val Gly Glu Leu Arg Glu Ser Asn Ser
        195                 200                 205

Gly Ala Glu Asn Thr Thr Glu Thr Gln Thr Ser Thr Ser Thr Ser Ser
    210                 215                 220

Leu Arg Ser Asp Pro Lys Leu Trp Leu Ala Leu Gly Thr Val Ala Thr
225                 230                 235                 240

Gly Leu Ile Gly Leu Ala Ala Thr Gly Ile Val Gln Ala Leu Ala Leu
                245                 250                 255

Thr Pro Glu Pro Asp Ser Pro Thr Thr Thr Asp Pro Asp Ala Ala Ala
            260                 265                 270

Ser Ala Thr Glu Thr Ala Thr Arg Asp Gln Leu Thr Lys Glu Ala Phe
        275                 280                 285

Gln Asn Pro Asp Asn Gln Lys Val Asn Ile Asp Glu Leu Gly Asn Ala
    290                 295                 300

Ile Pro Ser Gly Val Leu Lys Asp Asp Val Val Ala Asn Ile Glu Glu
305                 310                 315                 320
```

```
Gln Ala Lys Ala Ala Gly Glu Ala Lys Gln Gln Ala Ile Glu Asn
            325                 330                 335
Asn Ala Gln Ala Gln Lys Lys Tyr Asp Glu Gln Gln Ala Lys Arg Gln
            340                 345                 350
Glu Glu Leu Lys Val Ser Ser Gly Ala Gly Tyr Gly Leu Ser Gly Ala
        355                 360                 365
Leu Ile Leu Gly Gly Ile Gly Val Ala Val Thr Ala Ala Leu His
        370                 375                 380
Arg Lys Asn Gln Pro Val Glu Gln Thr Thr Thr Thr Thr Thr Thr
385                 390                 395                 400
Thr Thr Thr Ser Ala Arg Thr Val Glu Asn Lys Pro Ala Asn Asn Thr
            405                 410                 415
Pro Ala Gln Gly Asn Val Asp Thr Pro Gly Ser Glu Asp Thr Met Glu
            420                 425                 430
Ser Arg Arg Ser Ser Met Ala Ser Thr Ser Ser Thr Phe Phe Asp Thr
        435                 440                 445
Ser Ser Ile Gly Thr Val Gln Asn Pro Tyr Ala Asp Val Lys Thr Ser
    450                 455                 460
Leu His Asp Ser Gln Val Pro Thr Ser Asn Ser Asn Thr Ser Val Gln
465                 470                 475                 480
Asn Met Gly Asn Thr Asp Ser Val Val Tyr Ser Thr Ile Gln His Pro
            485                 490                 495
Pro Arg Asp Thr Thr Asp Asn Gly Ala Arg Leu Leu Gly Asn Pro Ser
            500                 505                 510
Ala Gly Ile Gln Ser Thr Tyr Ala Arg Leu Ala Leu Ser Gly Gly Leu
        515                 520                 525
Arg His Asp Met Gly Gly Leu Thr Gly Gly Ser Asn Ser Ala Val Asn
        530                 535                 540
Thr Ser Asn Asn Pro Pro Ala Pro Gly Ser His Arg Phe Val
545                 550                 555

<210> SEQ ID NO 12
<211> LENGTH: 485
<212> TYPE: PRT
<213> ORGANISM: Escherichia coli

<400> SEQUENCE: 12

Asn Ser Val Ala Asp Ala Ala Asp Ser Arg Ala Ser Asp Ile Pro Gly
1               5                   10                  15
Leu Pro Thr Asn Pro Leu Arg Phe Ala Ala Ser Glu Val Ser Leu His
            20                  25                  30
Gly Ala Leu Glu Val Leu His Asp Lys Gly Gly Leu Asp Thr Leu Asn
        35                  40                  45
Ser Ala Ile Gly Ser Ser Leu Phe Arg Val Glu Thr Arg Asp Asp Gly
    50                  55                  60
Ser His Val Ala Ile Gly Gln Lys Asn Gly Leu Glu Thr Thr Val Val
65                  70                  75                  80
Leu Ser Glu Gln Glu Phe Ser Ser Leu Gln Ser Leu Asp Pro Glu Gly
            85                  90                  95
Lys Asn Lys Phe Val Phe Thr Gly Gly Arg Gly Gly Pro Gly His Ala
            100                 105                 110
Met Val Thr Val Ala Ser Asp Ile Ala Glu Ala Arg Gln Arg Ile Ile
        115                 120                 125
Asp Lys Leu Glu Pro Lys Asp Thr Lys Glu Thr Lys Glu Pro Gly Asp
```

```
            130                 135                 140
Pro Asn Ser Gly Glu Gly Lys Ile Ile Glu Ile His Thr Ser Thr Ser
145                 150                 155                 160

Thr Ser Ser Leu Arg Ala Asp Pro Lys Leu Trp Leu Ser Leu Gly Thr
                165                 170                 175

Ile Ala Ala Gly Leu Ile Gly Met Ala Ala Thr Gly Ile Ala Gln Ala
                180                 185                 190

Val Ala Leu Thr Pro Glu Pro Asp Asp Pro Ile Thr Thr Asp Pro Asp
                195                 200                 205

Ala Ala Ala Asn Thr Ala Glu Ala Ala Lys Asp Gln Leu Thr Lys
210                 215                 220

Glu Ala Phe Gln Asn Pro Asp Asn Gln Lys Val Asn Ile Asp Glu Asn
225                 230                 235                 240

Gly Asn Ala Ile Pro Ser Gly Glu Leu Lys Asp Asp Val Val Ala Gln
                245                 250                 255

Ile Ala Glu Gln Ala Lys Ala Ala Gly Glu Gln Ala Arg Gln Glu Ala
                260                 265                 270

Ile Glu Ser Asn Ser Gln Ala Gln Gln Lys Tyr Asp Glu Gln His Ala
                275                 280                 285

Lys Arg Glu Gln Glu Met Ser Leu Ser Ser Gly Val Gly Tyr Gly Ile
                290                 295                 300

Ser Gly Ala Leu Ile Leu Gly Gly Gly Ile Gly Ala Gly Val Thr Ala
305                 310                 315                 320

Ala Leu His Arg Lys Asn Gln Pro Ala Glu Gln Thr Ile Thr Thr Arg
                325                 330                 335

Thr Val Val Asp Asn Gln Pro Thr Asn Asn Ala Ser Ala Gln Gly Asn
                340                 345                 350

Thr Asp Thr Ser Gly Pro Glu Glu Ser Pro Ala Ser Arg Arg Asn Ser
                355                 360                 365

Asn Ala Ser Leu Ala Ser Asn Gly Ser Asp Thr Ser Ser Thr Gly Thr
                370                 375                 380

Val Glu Asn Pro Tyr Ala Asp Val Gly Met Pro Arg Asn Asp Ser Leu
385                 390                 395                 400

Ala Arg Ile Ser Glu Glu Pro Ile Tyr Asp Glu Val Ala Ala Asp Pro
                405                 410                 415

Asn Tyr Ser Val Ile Gln His Phe Ser Gly Asn Ser Pro Val Thr Gly
                420                 425                 430

Arg Leu Val Gly Thr Pro Gly Gln Gly Ile Gln Ser Thr Tyr Ala Leu
                435                 440                 445

Leu Ala Ser Ser Gly Leu Arg Leu Gly Met Gly Gly Leu Thr Gly
450                 455                 460

Gly Gly Glu Ser Ala Val Ser Thr Ala Asn Ala Ala Pro Thr Pro Gly
465                 470                 475                 480

Pro Ala Arg Phe Val
                485

<210> SEQ ID NO 13
<211> LENGTH: 1920
<212> TYPE: DNA
<213> ORGANISM: Escherichia coli

<400> SEQUENCE: 13
cggctgcata ccgttacgtc atagtaatat aaaggaacgt gtcaaatttc taaataaaag    60
gatatatgta tgcctattgg taaccttggt aataatgtaa atggcaatca tttaattccc   120
```

-continued

```
cctgcgccgc cactaccttc acaaacagac ggcgcggcac ggggaggaac tggtcatcta      180
attagctcta caggagcatt aggatctcgt tcattgtttt ctcccctgag aaattctatg      240
gctgattctg tcgattccag agatattcca ggacttccta caaacccatc gaggcttgct      300
gcagctacat ctgagacatg cttgcttgga ggatttgaag ttctccatga taaggggcca      360
cttgatattc tcaatacgca aattggaccc tctgcatttc gtgttgaagt gcaggcagat      420
ggtactcatg ccgctattgg agaaaaaaat ggtttggagg ttagcgttac attaagtcct      480
caagaatgga gcagcttgca atctattgat actgagggta aaaacagatt tgttttacc       540 gggggacgtg gcggtagtgg gcatccgatg gtcactgtcg catcagatat cgcggaagct      600
cgtacgaaaa tactggccaa attagaccca gacaatcatg gaggacgtca acccaaggac      660
gttgatacgc gttctgttgg tgttggcagc gcttcgggaa tagatgatgg cgttgttagc      720 gaaaccata  cttcaacaac aaattccagc gttcgctcag atcctaaatt ctgggtttct       780
gtcggcgcaa ttgctgctgg tttagcggga ctggcggcaa ctggtattgc acaggcgttg      840
gctttgacac cggaaccgga tgatcctaca accaccgatc ctgatcaggc cgcaaatgct      900
gcagaaagtg caacaaaaga tcagttaacg caagaagcat tcaagaaccc tgagaaccag      960
aaagttaaca tcgatgcgaa cggaaatgct attccgtctg gggaattaaa agatgatatt      1020
gttgagcaaa tagcacaaca agctaaagag gctggtgagg tggccagaca gcaggctgtt      1080
gaaagcaatg cacaggcgca gcagcgatat gaggatcagc atgccagacg tcaggaggaa      1140
ttacagcttt catcgggtat tggttacggc ctcagcagtg cattgattgt tgctggggga      1200
attggtgctg gtgtaacgac tgcgctccat agacgaaatc agccggcaga acagacaact      1260
actacaacaa cacatacggt agtgcagcaa cagaccggag ggataccca  gcacaaggtg      1320 gcactgatgc cacaagagcg aagacgcttc tctgatagac gtgattcgca ggggagtgtt      1380
gcatcgacac actggtcaga ttcctctagc gaagtggtta atccatatgc tgaagttggg      1440
ggggctcgga atagtctatc ggctcatcag ccagaagagc atatttatga tgaggtcgct      1500
gcagatcctg gttatagcgt tattcagaat ttttcaggga gcggcccagt taccggaagg      1560
ttaataggaa ctccagggca aggtatccaa agtacttatg cgcttctggc aaacagcggc      1620
ggattgcgtt taggtatggg aggattaacg agtggtggcg agacggcagt aagttctgta      1680
aatgccgcac caacgccggg accagtacgt ttcgttttaaa tatatctgtg agtatttagt      1740
tgaggttggg gtggggtggg ggggcgtttt actagcgtta atgtttcaga gaacaacgtt      1800
gcagcatggg taactcttga acttctgtta ttataatcaa ttaagagaaa ttataatgtc      1860
atcaagatct gaactttat  tagataggtt tgcggaaaaa attggtgttg gatctatttc      1920
```

<210> SEQ ID NO 14
<211> LENGTH: 571
<212> TYPE: PRT
<213> ORGANISM: Escherichia coli

<400> SEQUENCE: 14

Met Pro Ile Gly Asn Leu Gly Asn Asn Val Asn Gly Asn His Leu Ile
1               5                   10                  15

Pro Pro Ala Pro Pro Leu Pro Ser Gln Thr Asp Gly Ala Ala Arg Gly
            20                  25                  30

Gly Thr Gly His Leu Ile Ser Ser Thr Gly Ala Leu Gly Ser Arg Ser
        35                  40                  45

Leu Phe Ser Pro Leu Arg Asn Ser Met Ala Asp Ser Val Asp Ser Arg

```
                50                  55                  60
Asp Ile Pro Gly Leu Pro Thr Asn Pro Ser Arg Leu Ala Ala Ala Thr
 65                  70                  75                  80

Ser Glu Thr Cys Leu Leu Gly Gly Phe Glu Val Leu His Asp Lys Gly
                 85                  90                  95

Pro Leu Asp Ile Leu Asn Thr Gln Ile Gly Pro Ser Ala Phe Arg Val
                100                 105                 110

Glu Val Gln Ala Asp Gly Thr His Ala Ala Ile Gly Glu Lys Asn Gly
            115                 120                 125

Leu Glu Val Ser Val Thr Leu Ser Pro Gln Glu Trp Ser Ser Leu Gln
130                 135                 140

Ser Ile Asp Thr Glu Gly Lys Asn Arg Phe Val Phe Thr Gly Gly Arg
145                 150                 155                 160

Gly Gly Ser Gly His Pro Met Val Thr Val Ala Ser Asp Ile Ala Glu
                165                 170                 175

Ala Arg Thr Lys Ile Leu Ala Lys Leu Asp Pro Asp Asn His Gly Gly
            180                 185                 190

Arg Gln Pro Lys Asp Val Asp Thr Arg Ser Val Gly Val Gly Ser Ala
            195                 200                 205

Ser Gly Ile Asp Asp Gly Val Val Ser Glu Thr His Thr Ser Thr Thr
210                 215                 220

Asn Ser Ser Val Arg Ser Asp Pro Lys Phe Trp Val Ser Val Gly Ala
225                 230                 235                 240

Ile Ala Ala Gly Leu Ala Gly Leu Ala Ala Thr Gly Ile Ala Gln Ala
                245                 250                 255

Leu Ala Leu Thr Pro Glu Pro Asp Asp Pro Thr Thr Thr Asp Pro Asp
                260                 265                 270

Gln Ala Ala Asn Ala Ala Glu Ser Ala Thr Lys Asp Gln Leu Thr Gln
            275                 280                 285

Glu Ala Phe Lys Asn Pro Glu Asn Gln Lys Val Asn Ile Asp Ala Asn
            290                 295                 300

Gly Asn Ala Ile Pro Ser Gly Glu Leu Lys Asp Asp Ile Val Glu Gln
305                 310                 315                 320

Ile Ala Gln Gln Ala Lys Glu Ala Gly Glu Val Ala Arg Gln Gln Ala
                325                 330                 335

Val Glu Ser Asn Ala Gln Ala Gln Gln Arg Tyr Glu Asp Gln His Ala
            340                 345                 350

Arg Arg Gln Glu Glu Leu Gln Leu Ser Ser Gly Ile Gly Tyr Gly Leu
            355                 360                 365

Ser Ser Ala Leu Ile Val Ala Gly Gly Ile Gly Ala Gly Val Thr Thr
370                 375                 380

Ala Leu His Arg Arg Asn Gln Pro Ala Glu Gln Thr Thr Thr Thr Thr
385                 390                 395                 400

Thr His Thr Val Val Gln Gln Gln Thr Gly Ile Pro Gln His Lys
                405                 410                 415

Val Ala Leu Met Pro Gln Glu Arg Arg Arg Phe Ser Asp Arg Arg Asp
                420                 425                 430

Ser Gln Gly Ser Val Ala Ser Thr His Trp Ser Asp Ser Ser Ser Glu
            435                 440                 445

Val Val Asn Pro Tyr Ala Glu Val Gly Gly Ala Arg Asn Ser Leu Ser
            450                 455                 460

Ala His Gln Pro Glu Glu His Ile Tyr Asp Glu Val Ala Ala Asp Pro
465                 470                 475                 480
```

-continued

```
Gly Tyr Ser Val Ile Gln Asn Phe Ser Gly Ser Gly Pro Val Thr Gly
            485                 490                 495

Arg Leu Ile Gly Thr Pro Gly Gln Gly Ile Gln Ser Thr Tyr Ala Leu
            500                 505                 510

Leu Ala Asn Ser Gly Gly Leu Arg Leu Gly Met Gly Gly Leu Thr Ser
        515                 520                 525

Gly Gly Glu Thr Ala Val Ser Ser Val Asn Ala Ala Pro Thr Pro Gly
        530                 535                 540

Pro Val Arg Phe Val Met Ser Ser Arg Ser Glu Leu Leu Leu Asp Arg
545                 550                 555                 560

Phe Ala Glu Lys Ile Gly Val Gly Ser Ile Ser
                565                 570
```

HOST RECEPTOR FOR PATHOGENIC BACTERIA

The present application claims priority of U.S. application Ser. No. 60/065,130, filed on Nov. 12, 1997, which disclosure is incorporated herein by reference.

FIELD OF THE INVENTION

The present invention relates generally to the virulence of pathogenic organisms and more specifically to virulence factors associated with attaching and effacing pathogens, such as enteropathogenic and enterohemorrhagic *E. coli*.

BACKGROUND OF THE INVENTION

Enteropathogenic *Escherichia coli* (EPEC) is a leading cause of infant diarrhea and was the first *E. coli* shown to cause gastroenteritis. EPEC continues to be a significant cause of infantile diarrhea in developing nations contributing to high morbidity and mortality. EPEC forms small microcolonies on the surface of infected epithelial cells followed by intimate contact and localized degeneration of the epithelial brush border microvilli, cumulating in an attaching and effacing (A/E) lesion. The A/E lesion (or pedestal) is associated with the assembly of highly organized cytoskeletal structures in epithelial cells immediately beneath the adherent bacteria that include the cytoskeletal components actin, α-actinin, myosin light chain, ezrin, and talin.

EPEC is a member of a group of pathogenic organisms, collectively known as attaching and effacing pathogens, that adhere to host cells and cause localized accumulation of host actin beneath adherent organisms. Pathogens in this group include enterohemorrhagic *E. coli* (EHEC, the causative agent of hemorrhagic colitis and hemolytic uremic syndrome) and several other human and animal pathogens, including *Citrobacter rodentium* and *Hafnia alvei*.

A three-stage model describes enteropathogenic *E. coli* pathogenesis. An initial localized adherence to epithelial cells, mediated by a type IV fimbria, is followed by the activation of host epithelial cell signal transduction pathways and intimate attachment to host epithelial cells. These final two steps are collectively known as attaching and effacing. The signal transduction in the host epithelial cells involves activation of host cell tyrosine kinase activity leading to tyrosine phosphorylation of a 90 kilodalton (kDa) host membrane protein, Hp90, and fluxes of intracellular inositol phosphate (IP$_3$) and calcium. Following this signal transduction, the bacteria adheres intimately to the surface of the epithelial cell, accompanied by damage to host epithelial cell microvilli and accumulation of cytoskeletal proteins beneath the bacteria.

Recently, some of the bacterial components involved in pedestal formation have been identified. EPEC possess a virulence plasmid which encodes the bundle forming pilus and a positive virulence factor regulator, Per. All of the genes which encode products that are necessary for pedestal formation are found within a 35 kilobase par (kb) pathogenicity island in the *E. coli* chromosome. Within the Locus of Enterocyte Effacement (LEE) region are several genes whose products have different functions, including a type III secretion apparatus proteins, secreted effector molecules and their chaperones, and intimin.

Type III secretion systems are being increasingly found in many pathogenic Gram-negative organisms, and the role of the EPEC type III secretion system is to secrete proteins necessary for formation of the A/E lesion. At least two proteins secreted by the EPEC secretion system, EspA and EspB, are necessary for activating EPEC induced signals in epithelial cells. These signals include calcium and inositol phosphate fluxes, and tyrosine phosphorylation of Hp90. Mutations in espA or espB, or those in the type III secretion system (sep and cfm), are unable to signal or induce binding of the EPEC adhesin intimin to epithelial cell surfaces.

Intimin is the product of a bacterial chromosomal LEE locus, eaeA, and is a 94 kDa EPEC outer membrane protein needed for intimate adherence. Mutants defective in eaeA form immature A/E lesions and do not organize phosphotyrosine proteins and cytoskeletal components beneath adherent bacteria, although epithelial signal transduction is still activated. Intimin participates in reorganization of the underlying host cytoskeleton after other bacterial factors (EspA and EspB) stimulate epithelial signal transduction.

Intimin binding to host cells also stimulates a second wave of signal transduction inside the mammalian cell, including tyrosine phosphorylation of phospholipase Cγ. In cultured cells intimin binds to the tyrosine phosphorylated form of Hp90, but only if mammalian cells have been preinfected with EPEC strains possessing an intact type II secretion system capable of secreting EspA and EspB. However, little was known about the identity of Hp90 other than it is tyrosine phosphorylated following EPEC infection and that it serves as a receptor for intimin. Phosphotyrosine proteins (presumably Hp90) are concentrated at the tip of the pedestal immediately beneath EPEC, but phosphotyrosine residues are not surface exposed in unpermeabilized cells. Biochemically, Hp90 behaves as an integral host membrane protein, and appears to be highly conserved. It also appears to play a key role in organizing polymerized actin under the adherent bacteria once it binds intimin.

SUMMARY OF THE INVENTION

The present invention is based on the discovery that a protein (Hp90) associated with pedestal formation in attaching and effacing bacteria, through its role as intimin receptor, is actually produced by the attaching and effacing bacteria. The present invention provides a polypeptide, called Tir (for translocated intimin receptor) which is secreted by pathogenic *E. coli*. Diagnosis of disease caused by pathogenic *E. coli* can be performed by standard techniques, such as those based upon the use of antibodies which bind to Tir to detect the protein, as well as those based on the use of nucleic acid probes for detection of nucleic acids encoding Tir polypeptide. The invention also provides isolated nucleic acid sequences encoding Tir polypeptide, Tir peptides, a recombinant method for producing recombinant Tir, antibodies which bind to Tir, and a kit for the detection of Tir-producing *E. coli*. The invention also provides a method of immunizing a host with Tir to induce a protective immune response to Tir. The invention further provides a method for screening for compounds which interfere with the binding of bacterial pathogens to their receptors.

In another aspect of the invention, fusion proteins are provided. In this embodiment, a polynucleotide encoding Tir is operably linked to a second polynucleotide encoding a polypeptide of interest. In a preferred embodiment, the second polynucleotide of interest encodes a polypeptide conferring an immune response, however, the Tir polypeptide can be linked to any second polypeptide of interest.

In another embodiment, the fusion proteins of the invention are delivered into a host cell.

Few mammalian receptors have been identified for bacterial adhesins and invasins. The discovery that Hp90, now designated Tir, is a bacterial protein was unexpected. All previous biochemical data indicated that it was a mammalian integral membrane protein. Several pathogenic Gram-negative bacteria use type III secretion systems to cause various effects in their host cells. EPEC represents the first pathogen that uses a type III system to insert a bacterial receptor into its host cell. Other pathogens may also use this strategy, especially for those in which the mammalian receptor has not been identified. Tir also represents the first bacterial protein that is tyrosine phosphorylated in host cells. Other virulence factors may be inserted into host cells by type III systems become modified inside the host cell.

BRIEF DESCRIPTION OF THE DRAWINGS

FIG. 1 shows that antibodies generated against the enteropathogenic E. coli (EPEC) 78 kilodalton (kDa) secreted protein recognize Hp90.

In FIG. 6B, two putative membrane spanning domains are underlined, and the 6 tyrosine residues are shaded. In FIG. 6B, the location of tir in Locus of Enterocyte Effacement (LEE) and the gene deletion strategy are diagramed.

FIG. 7 shows the T7 and HSV epitope tagging of Tir.

FIG. 8 shows that intimin binds Tir from EPEC.

FIGS. 9A–B shows the sequence similarity between Tir polypeptides from EPEC (SEQ ID NO: 10), EHEC (SEQ ID NO: 11) and RDEC-1: (SEQ ID NO: 12). SEQ ID NO: 12 is the deduced amino acid sequence of SEQ ID NO: 5.

DETAILED DESCRIPTION OF THE INVENTION

Figure 1A:
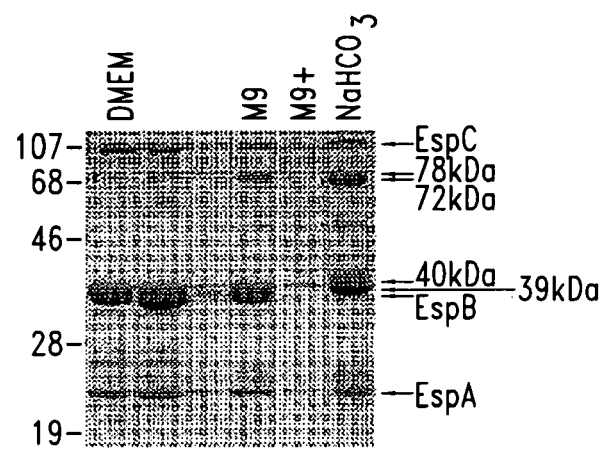
FIG. 1A shows the secreted 78 kDa protein found in EPEC growth supernatants.

The present invention provides a polypeptide, called Tir, which is secreted by attaching and effacing pathogens, such as the enteropathogenic (EPEC) and enterohemorrhagic (EHEC) *E. coli*. The present invention provides a polypeptide, called Tir (for translocated intimin receptor, which is secreted by pathogenic *E. coli*, such as the enteropathogenic (EPEC) and enterohemorrhagic (EHEC) *E. coli*. These bacterial pathogens insert their own receptors into mammalian cell surfaces, to which the bacterial pathogen then adheres to trigger additional host signaling events, such as actin nucleation. Diagnosis of disease caused by Tir-producing pathogens can be performed by standard techniques, such as those based upon the use of antibodies which bind to Tir to detect the protein, as well as those based on the use of nucleic acid probes for detection of nucleic acids encoding Tir polypeptide. The invention also provides isolated nucleic acid sequences encoding Tir polypeptide, Tir peptides, a recombinant method for producing recombinant Tir, antibodies which bind to Tir, and a kit for the detection of Tir-producing organisms. The invention also provides a method of immunizing a host with Tir to induce a protective immune response to Tir. The invention further provides a method for screening for compounds which interfere with the binding of Tir-producing pathogens to Tir.

The details of the preferred embodiments of the present invention are set forth in the accompanying drawings and the description below. Based on the details of the invention described herein, numerous additional innovations and changes will become obvious to one skilled in the art.

Tir Polypeptide

The invention provides a substantially purified translocated intimin receptor (Tir) polypeptide that binds intimin. As used herein, the term "Tir" (for translocated intimin receptor) refers to a secreted polypeptide that binds intimin.

The discovery that Hp90, now designated Tir, is a bacterial protein was unexpected. All previous biochemical data indicated that it was a mammalian integral membrane protein. The only means of detection was anti-PY antibodies. It had previously been assumed that in uninfected cells it was in the unphosphorylated form and thus undetectable. However, Tir was found in all EPEC infected mammalian cell types examined, and it behaved as a conserved protein.

Several lines of evidence now prove the bacterial origin of Tir. Firstly, polyclonal antibodies against the EPEC-secreted Tir protein recognize and immunodeplete membranes of Tir. Secondly, isoelectric focusing and fluorescence microscopy experiments with both PY and Tir antibodies demonstrate its identity. Thirdly, the identification and deletion of the EPEC tir gene, and generation of epitope tagged Tir fusion proteins, prove that the bacterial Tir protein becomes tyrosine phosphorylated and behaves as Hp90. Finally, intimin interacts directly and specifically with the secreted Tir protein from EPEC.

Tir delivery into host cells requires EspA, EspB, and the type III secretion apparatus. In strains lacking EspA and EspB a tyrosine phosphorylated Tir is not detectable in HeLa. Whether Tir delivery is sufficient to activate the other signals seen in EPEC infected cells (such as calcium and inositol phosphate fluxes, myosin light chain phosphorylation, actin rearrangement), or whether EspA and EspB mediate these signals via additional mechanisms remains to be resolved. These various processes can not be uncoupled at present. Upon contact with epithelial cells, EspB adopts a protease resistant form associated with epithelial membranes, which may facilitate Tir delivery into the host cell membrane.

Tir has at least three identified functions. One function is as the EPEC intimin receptor on mammalian cell surfaces, binding intimin on the bacterial surface. This binding, at least under the in vitro conditions described here, does not require tyrosine phosphorylation as the intimin fusion protein His-T7Int bound the bacterial secreted unphosphorylated form of Tir in a specific manner. Strains lacking EspA, EspB, or Tir are unable to induce intimin-mediated binding which is needed for intimate adherence, presumably because they are unable to deliver Tir to the host cell surface. Several lines of evidence show that Tir is located in the plasma membrane and functions an integral epithelial membrane protein. Intimin fusion protein only binds to fixed epithelial cells that have been preinfected with EPEC strains that deliver Tir to the host cell suggesting that Tir is surface exposed. Tir co-localizes with the epithelial cell membrane extracts and cannot be extracted with high salt from these extracts. It is unlikely that Tir is in another membrane, given its co-localization beneath adherent bacteria at the cell surface (FIG. 4) and its ability to bind intimin. Tir is sensitive to limited surface proteolysis in unpermeabilized cells. Fluorescence microscopy data demonstrated that anti-EPEC 78 kilodalton (kDa) antibodies only bind to unpermeabilized membranes of intimin-mutant infected cells, but not tir infected or uninfected cells, also supporting a plasma membrane surface exposed location. Finally, phosphotyrosine antibodies only recognize Tir in permeabilized cells, indicating a transepithelial membrane orientation with tyrosine phosphorylated residues at the cytoplasmic face.

A second function of Tir is to nucleate actin following intimin binding. Strains lacking intimin or Tir are unable to localize actin beneath adherent bacteria, although there is a pronounced accumulation of actin in the general vicinity of bound bacteria. Given that Tir is located at the tip of the pedestal within mammalian cells, and that if the Tir-intimin linkage does not occur actin is not organized beneath bacteria, it is likely that Tir is involved in linking actin either directly or indirectly to the host membrane thereby forming the pedestal.

A third function of Tir (which is probably related to the actin organization) deals with transmitting additional signals to host cells once the Tir-intimin interaction occurs. Intimin mediated binding to epithelial cells triggers tyrosine phosphorylation of phospholipase Cγ and other host proteins. These signals follow Tir phosphorylation and other early signal events and intimin binding. Few actin-membrane linking proteins have been identified, and Tir represents a novel candidate for such a function, given its bacterial origin. However, two other bacterial molecules from pathogenic *Listeria monocytogenes* and *Shigella* species, ActA and IcsA, are capable of nucleating actin through various cytoskeletal crosslinkers, albeit from a cytoplasmic location. However, EPEC induced cytoskeletal structures are more reminiscent of microvilli and, thus, EPEC affords a unique model to study the assembly of such structures.

Figure 8A:
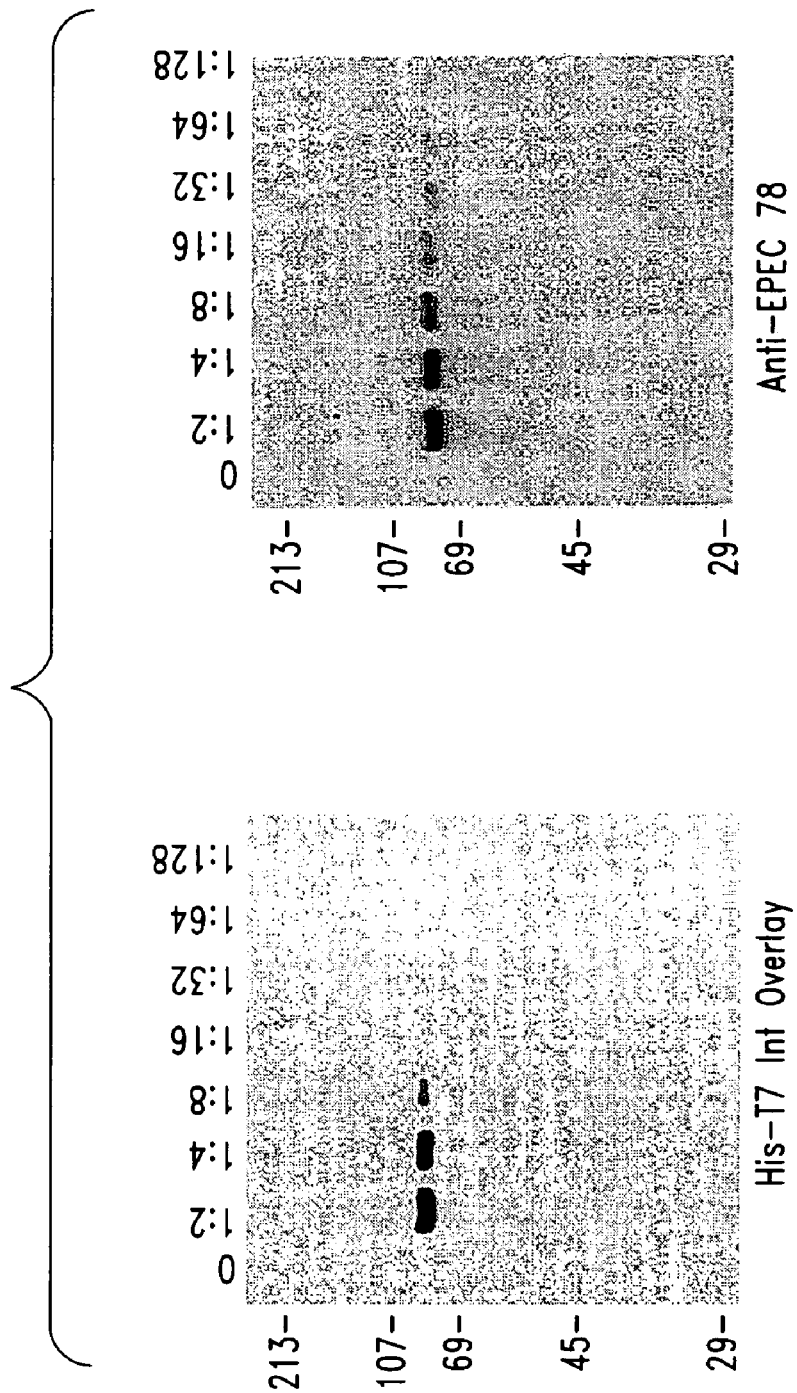
FIG. 8A shows that the His-T7Int protein specifically bound to a single 78 kDa band, subsequently identified as Tir by probing the same blot with anti-EPEC 78 kDa antibodies. This binding occurred in a concentration dependant manner. Using gel overlay systems, various intimin fusion proteins only bind to Tir but not to the larger molecular weight P, integrins (or any other epithelial membrane molecule). EPEC or tir growth supernatants were isolated, 2-fold serial dilutions made and each doped with equal amounts of HeLa membrane extracts. Samples were resolved by 12% SDS-PAGE and transferred to nitrocellulose in duplicate prior to overlaying with 130 µg of His-T7Int fusion protein and probing with T7 specific antibodies (left panel). Following this, the same blot was reacted with anti-EPEC 78 kDa antibodies (right panel). Dilutions are indicated at top of gels with position of molecular mass markers on the side.

An unexpected result of this invention is the discovery that intimin does not bind to $\beta_1$ integrins. The 280 C-terminal residues of intimin do not bind to $\beta_1$ integrins. Binding of MBP-Int (the construction of which is described in EXAMPLE VII) to epithelial cells had been detected when the cells have been preinfected with EPEC, but not to uninfected cells or those infected with type II secretion or signaling mutants, cells which still express $\beta_1$ integrins. However, when MBP-Int is used to precipitate the 90 kDa form of Tir from epithelial membranes, $\beta_1$ integrins are not co-precipitated, despite their presence in the epithelial membrane extract used for precipitations. Additionally, using gel overlay systems (described in EXAMPLE VII), various intimin fusion proteins only bind to Tir but not to the larger molecular weight $\beta_1$ integrins or any other epithelial membrane molecule (FIG. 8A). These results show that Tir, and not $\beta_1$ integrins, is the main intimin receptor on cultured mammalian cells.

The Tir polypeptide provided by the invention may be produced by any organism. Specifically, the Tir polypeptide provided by the invention may be produced by bacteria. Several pathogenic Gram-negative bacteria use type III secretion systems to cause various effects in their host cells. EPEC represents only the first pathogen that uses a type III system to insert a bacterial receptor into its host cell. Other pathogens are expected to use this strategy, especially those pathogens in which the mammalian receptor has not been identified. Tir also represents the first bacterial protein that is tyrosine phosphorylated in host cells. Other virulence factors are expected to inserted into host cells by type III systems, possibly later becoming modified inside the host cell. EPEC is a member of a group of related pathogens that cause A/E lesions. Given the similarity of the various intimins, EspA, EspB, and the type III secretion systems found in these pathogens, it is expected that attaching and effacing pathogens follow a similar strategy for mediating intimate adherence. Indeed, reported sequences upstream of orfU from EPEC, RDEC and *Citrobacter* strains have partial open reading frames homologous to the C-terminal sequence of EPEC Tir.

The Tir polypeptide provided by the invention may be produced by Gram-negative bacteria. The Gram-negative bacteria are a diverse group of organisms and include Spirochaetes such as *Treponema* and *Borrelia*, Gram-negative bacilli including the Pseudomonadaceae, Legionellaceae, Enterobacteriaceae, Vibrionaceae, Pasteurellaceae, Gram-negative cocci such as Neisseriaceae, anaerobic *Bacteroides*, and other Gram-negative bacteria including *Rickettsia, Chlamydia*, and *Mycoplasma*.

Gram-negative bacilli (rods) are important in clinical medicine. They include (1) the Enterobacteriaceae, a family which comprises many important pathogenic genera, (2) *Vibrio, Campylobacter* and *Helicobacter* genera, (3) opportunistic organisms (e.g., *Pseudomonas, Flavobacterium*, and others) and (4) *Haemophilus* and *Bordetella* genera. The Gram-negative bacilli are the principal organisms found in infections of the abdominal viscera, peritoneum, and urinary tract, as well secondary invaders of the respiratory tracts, burned or traumatized skin, and sites of decreased host resistance. Currently, they are the most frequent cause of life-threatening bacteremia. Examples of pathogenic Gram-negative bacilli are *E. coli* (diarrhea, urinary tract infection, meningitis in the newborn), *Shigella* species (dysentery), *Salmonella typhi* (typhoid fever), *Salmonella typhimurium* (gastroenteritis), *Yersinia enterocolitica* (enterocolitis), *Yersinia pestis* (black plague), *Vibrio cholerae* (cholera), *Campylobacter jejuni* (enterocolitis), *Helicobacter jejuni* (gastritis, peptic ulcer), *Pseudomonas aeruginosa* (opportunistic infections including burns, urinary tract, respiratory tract, wound infections, and primary infections of the skin, eye and ear), *Haemophilus influenzae* (meningitis in children, epiglottitis, otitis media, sinusitis, and bronchitis), and *Bordetella pertussis* (whooping cough). *Vibrio* is a genus of motile, Gram-negative rod-shaped bacteria (family Vibrionaceae). *Vibrio cholerae* causes cholera in humans; other species of *Vibrio* cause animal diseases. *E. coli* colonize the intestines of humans and warm blooded animals, where they are part of the commensal flora, but there are types of *E. coli* that cause human and animal intestinal diseases. They include the enteroaggregative *E. coli* (EaggEC), enterohaemorrhagic *E. coli* (EHEC), enteroinvasive *E. coli* (EIEC), enteropathogenic *E. coli* (EPEC) and enterotoxigenic *E. coli* (ETEC). Uropathogenic *E. coli* (UPEC) cause urinary tract infections. There are also neonatal meningitis *E. coli* (NMEC). Apart from causing similar infections in animals as some of the human ones, there are specific animal diseases including: calf septicaemia, bovine mastitis, porcine oedema disease, and air sac disease in poultry.

A homologous tir gene in EHEC (SEQ ID NO:3) has been cloned. However, EHEC does not cause tyrosine phosphorylation of its receptor, indicating differences between these two pathogens. The invention thus provides a useful scientific method to investigate pathogenesis by cell biology.

The fact that EPEC Tir, but not EHEC Tir, is tyrosine phosphorylated provides a method to differentiate these two pathogens that contain very similar virulence factors. Thus, bacteria may be probed with anti-phosphotyrosine and anti-Tir antibodies. As used herein, "anti-phosphotyrosine" antibodies are those antibody which bind to an epitope, wherein the epitope has a phosphorylated tyrosine. Anti-phosphotyrosine antibodies bind to proteins with phosphorylated tyrosine but not to tyrosine which is not phosphorylated.

Detection of binding of anti-phosphotyrosine and tir antibodies to bacteria may be either by immunofluorescence or Western blots. EPEC will be positive for both anti-phosphotyrosine and anti-Tir binding. EHEC will be positive for both anti-Tir binding and negative for anti-phosphotyrosine binding.

The pathogenic bacteria in the Gram-negative aerobic cocci group include *Neisseria, Moraxella (Branhamella)*, and the *Acinetobacter*. The genus *Neisseria* includes two important human pathogens, *Neisseria gonorrhoeae* (urethritis, cervicitis, salpingitis, proctitis, pharyngitis, conjunctivitis, pharyngitis, pelvic inflammatory disease, arthritis, disseminated disease) and *Neisseria meningitides*(meningitis, septicemia, pneumonia, arthritis, urethritis). Other Gram-negative aerobic cocci that were previously considered harmless include *Moraxella (Branhamella) catarrhalis* (bronchitis and bronchopneumonia in patients with chronic pulmonary disease, sinusitis, otitis media) has recently been shown to be an common cause of human infections.

The Tir polypeptide provided by the invention may be secreted by Gram-negative bacteria through the type III secretion system. Gram-negative bacteria utilize specialized machinery to export molecules across their two membranes, a process critical for moving virulence factors to the bacterial surface where they can interact with host components. Gram-negative secretion has been divided into four major pathways. First, the Type I secretion is used by a small family of toxins, with *E. coli* hemolysin being the prototype. Second, the type II secretion system is the major export pathway used by most Gram-negative bacteria to export many molecules, including some virulence factors; it shares homology to mammalian drug resistance mechanisms. Third, the type IV secretion system is encoded within the secreted product, which cleaves itself as part of the secretion mechanism; the prototype of this system is the *Neisseria* IgA protease. Fourth, the most recently discovered secretion pathway, is the type III pathway.

Type III secretion systems were originally described as a secretion system for *Yersinia* secreted virulence proteins, YOPs, which are critical for *Yersinia* virulence. A homologous secretion system was then identified in several plant pathogens, including *Pseudomonas syringae, P. solanacearurn*, and *Xantharmonas carnpestris*. These plant pathogens use this secretion pathway to secrete virulence factors (harpins and others) that are required for causing disease in plants. Although the secretion system is similar, harpins and YOPs (i.e. the secreted virulence factors) are not homologous polypeptides. Several other type III secretion systems necessary for virulence have more recently been identified in other pathogens. These systems include the invasion systems *Salmonella* and *Shigella* use to enter cells and cause disease. Another type III secretion system has been identified in *Salmonella* which is critical for disease, although the secreted products of this pathway and the virulence mechanisms have not been established yet. *Pseudomonas aeruginosa* has a type II secretion system necessary for secretion of Exoenzyme S, a potent virulence factor.

In one embodiment, Tir polypeptide may be secreted by an attaching and effacing (A/E) pathogen, such as EPEC or EHEC. Tir from EPEC is necessary for activating epithelial cell signal transduction, intimate contact, and formation of attaching and effacing lesions, processes correlated with disease. Examples of epithelial cells are cells of the intestines, cells of the HeLa cell line, and cells of the J774 cell line.

In one embodiment, Tir has a molecular weight of about 78 kDa as determined by SDS-PAGE, but when obtained from epithelial cells (Hp90) has a molecular weight of about 90 kDa as determined by SDS-PAGE. Although the Tir protein secreted from EPEC is predicted to encode a 56.8 kDa protein, a molecular mass of about 78 kDa was observed for the secreted protein, which may reflect some additional bacterial modification or abnormal migration due to amino acid composition or structural features. Tir is predicted to have two transmembrane domains with the six tyrosine residues, potential kinase substrates, in the C-terminal half.

Tir polypeptides included in the invention can have one of the amino acid sequences of Tir from pathogenic *E. coli*, for example, the amino acid sequence of SEQ ID NO:10 and SEQ ID NO:11.

As used herein, the term "polypeptide" encompasses any naturally occurring allelic variant thereof as well as manufactured recombinant forms. Tir polypeptides encompass both naturally occurring and recombinant forms, i.e., non-naturally occurring forms of the protein and the peptide that are sufficiently identical to naturally occurring Tir peptide to have a similar function of binding to the intimin or intimin-like receptor. Examples of such polypeptides include the Tir polypeptides from enteropathogenic and enterohemorrhagic *E. coli*, but are not limited to them. Protein and polypeptides include derivatives, analogs and peptidomimetics and fusion proteins. Alternatively, Tir peptides can be chemically synthesized using synthesis procedures known to one skilled in the art. Preferably, an automated peptide synthesizer is used with $N^\alpha$Fmoc amino acids on a polyethylene glycol-polystyrene (PEGPS) graft resin. Suitable linkers such as a peptide amide linker (PAL) can be used, for example, to create carboxamide end groups.

Fragments of Tir are also useful, in addition to the full-length polypeptide sequence of Tir. The invention also includes fragments of Tir polypeptides that retain at least one Tir-specific activity or epitope. For example, a Tir polypeptide fragment containing, e.g., at least 8–10 amino acids can be used as an immunogen in the production of Tir-specific antibodies. The fragment can contain, for example, an amino acid sequence that is conserved in Tir. Different fragments of Tir are useful in raising an immune response to Tir-producing pathogens. For example, different antibodies to different fragments of Tir are useful for blocking different interactions between Tir and other molecules, such as intimin. It is well-known to those of skill in the immunological arts that a set of antibodies to different aspects of a molecule are more useful than a single antibody to one aspect of the molecule. In addition to their use as peptide immunogens, the above-described Tir fragments can be used in immunoassays, such as ELISAs, to detect the presence of Tir-specific antibodies in samples. Furthermore, fragments of Tir are useful in interfering with the binding between full-length Tir polypeptide and intimin. A method of screening for Tir polypeptide and other compounds which interfere with the binding of Tir polypeptide and intimin is described infra.

Additionally, the Tir polypeptide or fragments thereof which retain the biological property of allowing delivery to a host cell may prove useful as a delivery mechanism for fusion proteins. As mentioned above, Tir is inserted into host cell membranes by EPEC. Given that Tir eventually resides in host cells, this raises the opportunity to exploit Tir as a delivery system for foreign fusion proteins fused to Tir to be delivered into host cells. This system can be used to alter the immune response to foreign proteins, for example a cell mediated/T cell response would be elicited by antigen fused to Tir and presented on the surface of cells, thus the antigen would be presented by a self or host cells rather than as a secreted protein. Alternatively, Tir can function as an adjuvant when fused to foreign sequences, thus eliciting a B-cell response, improving the immune response over peptides alone.

The term "substantially purified" is used herein to describe a molecule, such as a polypeptide (e.g., a Tir polypeptide, or a fragment thereof) that is substantially free of other proteins, lipids, carbohydrates, nucleic acids, and other biological materials with which it is naturally associated. For example, a substantially purified molecule, such as a polypeptide, can be at least 60%, by dry weight, the molecule of interest. One skilled in the art can purify Tir polypeptides using standard protein purification methods and the purity of the polypeptides can be determined using standard methods including, e.g., polyacrylamide gel electrophoresis (e.g., SDS-PAGE), column chromatography (e.g., high performance liquid chromatography (HPLC)), and amino-terminal amino acid sequence analysis.

Also included in the invention are polypeptides having sequences that are substantially identical to the sequence of a Tir polypeptide. A substantially identical amino acid sequence is a sequence that differs from a reference sequence only by conservative amino acid substitutions, for example, substitutions of one amino acid for another of the same class (e.g., substitution of one hydrophobic amino acid, such as isoleucine, valine, leucine, or methionine, for another, or substitution of one polar amino acid for another, such as substitution of arginine for lysine, glutamic acid for aspartic acid, or glutamine for asparagine), or by one or more non-conservative substitutions, deletions, or insertions, provided that the polypeptide retains at least one Tir-specific activity or a Tir-specific epitope. For example, one or more amino acids can be deleted from a Tir polypeptide, resulting in modification of the structure of the polypeptide, without significantly altering its biological activity. For example, amino- or carboxyl-terminal amino acids that are not required for Tir biological activity, can be removed. Such modifications can result in the development of smaller active Tir polypeptides.

Other Tir polypeptides included in the invention are polypeptides having amino acid sequences that are at least 50% identical to the amino acid sequence of a Tir polypeptide, such as SEQ ID NO:10 and SEQ ID NO:11. The length of comparison in determining amino acid sequence homology can be, for example, at least 15 amino acids, for example, at least 20, 25, or 35 amino acids. Homology can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra).

The Tir polypeptides of the invention can be obtained using any of several standard methods. For example, Tir polypeptides can be produced in a standard recombinant expression systems (see below), chemically synthesized (this approach may be limited to small Tir peptide fragments), or purified from bacteria in which they are naturally expressed (see, e.g., Ausubel, et al., supra).

Polypeptides corresponding to one or more domains of the Tir polypeptide, truncated or deleted Tir polypeptides, as well as fusion proteins in which full length Tir proteins, polypeptides or derivatives (including fragments), or truncated Tir, are fused to an unrelated protein are also within the scope of the invention and can be designed on the basis of the tir nucleotide and Tir amino acid sequences disclosed in this section and the section above. The fusion protein may also be engineered to contain a cleavage site located between a Tir sequence and the non-Tir protein sequence, so that the Tir polypeptide may be cleaved away from the non-Tir moiety. Such fusion proteins or polypeptides include but are not limited to IgFc fusion which may stabilize the Tir protein in vivo; or fusion to an enzyme, fluorescent protein, a second polypeptide of interest or luminescent protein which provide a marker function. The polypeptide of interest may be an antigen to which it is desired to raise an immune response or to raise selective immunity.

Tir Polynucleotide

The invention also provides isolated polynucleotides that encode the Tir polypeptides described above, as well as fragments thereof. For example, isolated polynucleotides may encode the Tir polypeptides with the amino acid sequences of SEQ ID NO:10 and SEQ ID NO: 11. These polynucleotides can contain naturally occurring nucleotide sequences or sequences that differ from those of the naturally occurring nucleic acids that encode Tir, but encode the same amino acids, due to the degeneracy of the genetic code. The nucleic acids of the invention can contain DNA or RNA nucleotides, or combinations or modifications thereof.

By "isolated polynucleotide" is meant a polynucleotide, e.g., a DNA or RNA molecule, that is not immediately contiguous with the 5' and 3' flanking sequences with which it normally is immediately contiguous when present in the naturally occurring genome of the organism from which it is derived. The term thus describes, for example, a nucleic acid that is incorporated into a vector, such as a plasmid or viral vector; a nucleic acid that is incorporated into the genome of a heterologous cell (or the genome of a homologous cell, but at a site different from that at which it naturally occurs); and a nucleic acid that exists as a separate molecule, e.g., a DNA fragment produced by PCR amplification or restriction enzyme digestion, or an RNA molecule produced by in vitro transcription. The term also describes a recombinant nucleic acid that forms part of a hybrid gene encoding additional polypeptide sequences that can be used, for example, in the production of a fusion protein.

As used herein, the term "amplifying" refers to increasing the number of copies of a specific polynucleotide. For example, polymerase chain reaction (PCR) is method for amplifying a polynucleotide sequence using a polymerase and two oligonucleotide primers, one complementary to one of two polynucleotide strands at one end of the sequence to be amplified and the other complementary to the other of two polynucleotide strands at the other end. Because the newly synthesized DNA strands can subsequently serve as additional templates for the same primer sequences, successive rounds of primer annealing, strand elongation, and dissociation produce rapid and highly specific amplification of the desired sequence. PCR also can be used to detect the existence of the defined sequence in a DNA sample. In a specific embodiment, the invention provides a method for amplifying and thus detecting tir polynucleotide.

The nucleic acid molecules of the invention can be used as templates in standard methods for production of Tir gene products (e.g., Tir RNAs and Tir polypeptides; see below). In addition, the nucleic acid molecules that encode Tir polypeptides (and fragments thereof) and related nucleic acids, such as (1) nucleic acids containing sequences that are complementary to, or that hybridize to, nucleic acids encoding Tir polypeptides, or fragments thereof (e.g., fragments containing at least 12, 15, 20, or 25 nucleotides); and (2) nucleic acids containing sequences that hybridize to sequences that are complementary to nucleic acids encoding Tir polypeptides, or fragments thereof (e.g., fragments containing at least 12, 15, 20, or 25 nucleotides); can be used in methods focused on their hybridization properties. For example, as is described in further detail below, such nucleic acid molecules can be used in the following methods: PCR methods for synthesizing Tir nucleic acids, methods for detecting the presence of a Tir nucleic acid in a sample, screening methods for identifying nucleic acids encoding new Tir family members, and therapeutic methods.

The invention also includes methods for identifying nucleic acid molecules that encode members of the Tir polypeptide family in addition to Tir polypeptides shown in FIG. 9. In these methods, a sample, e.g., a nucleic acid library, such as a cDNA library, that contains a nucleic acid encoding a Tir polypeptide is screened with a Tir-specific probe, e.g., a Tir-specific nucleic acid probe. Tir-specific nucleic acid probes are nucleic acid molecules (e.g., molecules containing DNA or RNA nucleotides, or combinations or modifications thereof) that specifically hybridize to nucleic acids encoding Tir polypeptides, or to complementary sequences thereof. The term "Tir-specific probe," in the context of this method of invention, refers to probes that bind to nucleic acids encoding Tir polypeptides, or to complementary sequences thereof, to a detectably greater extent than to nucleic acids encoding other polypeptides, or to complementary sequences thereof. The term "Tir-specific probe" thus includes probes that can bind to nucleic acids encoding Tir polypeptides (or to complementary sequences thereof).

The invention facilitates production of Tir-specific nucleic acid probes. Methods for obtaining such probes can be designed based on the sequence similarities of polynucleotide sequences encoding Tir polypeptides, amino acid sequence alignments of which are shown in FIG. 9. The probes, which can contain at least 12, e.g., at least 15, 25, 35, 50, 100, or 150 nucleotides, can be produced using any of several standard methods (see, e.g., Ausubel, et al., supra). For example, preferably, the probes are generated using PCR amplification methods. In these methods, primers are designed that correspond to Tir-conserved sequences, which can include Tir-specific amino acids, and the resulting PCR product is used as a probe to screen a nucleic acid library.

Nucleotide sequences encoding Tir from EHEC (SEQ ID NO:3) were identified generally following this process based upon the analysis of the sequences of SEQ ID NO:1. The sequence similarities of the encoded protein to the Tir polypeptide of EPEC are shown in FIG. 9.

As is known in the art, PCR primers are typically designed to contain at least fifteen nucleotides, for example 15–30 nucleotides. The design of Tir-specific primers containing twenty-one nucleotides, which encode Tir peptides containing seven amino acids, are described as follows. Preferably, most or all of the nucleotides in such a probe encode Tir-conserved amino acids, including Tir-specific amino acids. For example, primers containing sequences encoding peptides containing at least 40% Tir-conserved amino acids can be used. Such a primer, containing twenty-one nucleotides, can include sequences encoding at least three Tir-conserved amino acids. Thus, the primer can contain sequences encoding at least one Tir-specific amino acid, for example, up to seven Tir-specific amino acids. Once Tir-specific amino acid sequences are selected as templates against which primer sequences are to be designed, the primers can be synthesized using, e.g., standard chemical methods. As is described above, due to the degeneracy of the genetic code, such primers should be designed to include appropriate degenerate sequences, as can readily be determined by one skilled in the art.

As used herein, the term "tir" refers to polynucleotide encoding the Tir polypeptide. These polynucleotides include DNA, cDNA and RNA sequences which encode Tir. All polynucleotides encoding all or a portion of Tir are also included herein. Such polynucleotides include naturally occurring, synthetic, and intentionally manipulated polynucleotides. For example, a tir polynucleotide can be subjected to site-directed mutagenesis. The tir polynucleotide sequence also includes antisense sequences. All degenerate nucleotide sequences are included in the invention as long as the amino acid sequence of Tir peptide encoded by the nucleotide sequence is functionally unchanged.

This invention encompasses nucleic acid molecules that hybridize to the polynucleotide of the invention. As used herein, the term "nucleic acid" encompasses RNA as well as single and double-stranded DNA and cDNA. The polynucleotide encoding Tir includes SEQ ID NO:1 and SEQ ID NO:3, as well as nucleic acid sequences complementary to that sequence. A complementary sequence may include an antisense nucleotide. When the sequence is RNA, the deoxynucleotides A, G, C, and T of SEQ ID NO:1 and SEQ ID NO:3 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein of SEQ ID NO:10 and SEQ ID NO:11 under physiological conditions.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

DNA sequences of the invention can be obtained by several methods. For example, the DNA can be isolated using hybridization techniques which are well known in the art. These include, but are not limited to (1) hybridization of libraries with probes to detect homologous nucleotide sequences, (2) polymerase chain reaction (PCR) on DNA using primers capable of annealing to the DNA sequence of interest, and (3) antibody screening of expression libraries to detect cloned DNA fragments with shared structural features.

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically or produced by fragmentation of the native sequence. Chemical synthesis requires that short, oligopeptide stretches of amino acid sequence be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. When used in combination with polymerase chain reaction technology, even rare expression products can be cloned.

The invention provides nucleic acid sequences encoding the Tir polypeptides, vectors and host cells containing them and methods of expression. After a peptide of Tir is isolated, nucleic acids encoding the peptide can be isolated by methods well known in the art. These isolated nucleic acids can be ligated into vectors and introduced into suitable host cells for expression. Methods of ligation and expression of nucleic acids within cells are well known in the art (see, Sambrook et al., *Molecular Cloning: A Laboratory Manual*, Cold Spring Harbor Laboratory, Cold Spring Harbor, N.Y., 1989, incorporated herein by reference). In EXAMPLE V, the primers MS102+(SEQ ID NO:8) and MS 103−(SEQ ID NO:9) were constructed by the use of such methods.

The invention provides vectors containing polynucleotides encoding the Tir polypeptide. As used herein, "vectors" includes plasmids, DNA and RNA viral vectors, baculoviral vectors, vectors for use in yeast, and other vectors well known to those of skill in the art. Several types of vectors are commercially available and can be used to practice this invention. Examples of vectors useful in the practice of this invention include those as widely varied as the low-copy vector pMW118, the positive-selection suicide vector pCVD442, and the commercially available pBluescript II SK(+) (Stragene, La Jolla, Calif.). For example, pCVD442, and pBluescript were used in EXAMPLE V.

When the vector is a plasmid, it generally contains a variety of components including promoters, signal sequences, phenotypic selection genes, origins of replication sites, and other necessary components as are known to those of skill in the art. Promoters most commonly used in prokaryotic vectors include the lacZ promoter system, the alkaline phosphatase phoA promoter, the bacteriophage λPL promoter (a temperature sensitive promotor), the tac promoter (a hybrid trp-lac promoter regulated by the lac repressor), the tryptophan promoter, and the bacteriophage T7 promoter. For example, the low-copy vector pMW118 is under the control of the lacZ promoter.

A signal sequence is typically found immediately 5' to the nucleic acid encoding the peptide, and will thus be transcribed at the amino terminus of the fusion protein.

Typical phenotypic selection genes are those encoding proteins that confer antibiotic resistance upon the host cell. For example, ampicillin resistance gene (amp) and the tetracycline resistance gene (tet) are readily employed for this purpose. For a different example, the aphA-3 cassette, encoding a gene for resistance to kanamycin (kan), may be cloned into the region of vector containing polynucleotides encoding the Tir polypeptide for selection of the vector on kanamycin plates.

Construction of suitable vectors containing polynucleotides encoding Tir polypeptide are prepared using standard recombinant DNA procedures well known to those of skill in the art. Isolated polynucleotides encoding the Tir polypeptide to be combined to form the vector are cleaved and ligated together in a specific order and orientation to generate the desired vector.

The invention provides a host cell containing a vector having a polynucleotide encoding the Tir polypeptide. The polynucleotides of the present invention can be used to produce transformed or transfected cells for enhanced production of the expressed Tir. Tir can be isolated from transformed cells by standard methods well known to those of skill in the art. The protein could be isolated, for example, using immunoaffinity purification.

DNA sequences encoding Tir can be expressed in vitro by DNA transfer into a suitable host cell. As used herein, "host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

The invention also provides a method for producing tir polynucleotide, where the tir polynucleotide sequences may be inserted into a recombinant expression vector. The term "recombinant expression vector" refers to a plasmid, virus or other vehicle known in the art that has been manipulated by insertion or incorporation of the Tir genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells.

Polynucleotide sequences encoding Tir can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

In bacterial systems, a number of expression vectors may be advantageously selected depending upon the use intended for the Tir gene product being expressed. For example, when a large quantity of such a protein is to be produced, for the generation of pharmaceutical compositions of Tir polypeptide or for raising antibodies to Tir polypeptide, for example, vectors which direct the expression of high levels of fusion protein products that are readily purified may be desirable. Such vectors include, but are not limited to the *E. coli* expression vector pUR278 (Ruther et al., 1983, *EMBO J.* 2:1791), in which the Tir gene product coding sequence may be ligated individually into the vector in frame with the lac z coding region that a fusion protein is produced; pIN vectors (Inouye & Inouye, 1985, *Nucleic Acids Res.* 13:3101–3109); and the like. pGEX vectors may also be used to express foreign polypeptide as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

An alternative fusion protein system allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

Transformation of a host cell with recombinant DNA may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired. For another example, triparental conjugation may be used to genetically introduce vector into E. coli. The transformed cells are selected by growth on an antibiotic, commonly tetracycline (tet) or ampicillin (amp), to which they are rendered resistant due to the presence of tet or amp resistance genes on the vector.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transformed with DNA sequences encoding the Tir of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. See for example, *Eukaryotic Viral Vectors*, Cold Spring Harbor Laboratory, Gluzman, ed. (1982).

Isolation and purification of microbial expressed polypeptide, or fragments thereof, provided by the invention, may be carried out by conventional means including preparative chromatography and immunological separations involving monoclonal or polyclonal antibodies.

Among the prokaryotic organisms which may serve as host cells are E. coli strain JM101, E. coli K12 strain 294 (ATCC number 31,446), E. coli strain W3110 (ATCC number 27,325), E. coli X1776 (ATCC number 31, 537), E. coli XL-1Blue (Stratagene), and E. coli B; however, many other strains of E. coli, such as HB101, NM522, NM538, NM539 and many other species and genera of prokaryotes can be used as well. Besides the E. coli strains listed above, bacilli such as *Bacillus subtillis*, other enterobacteriaceae such as *Salmonella typhimurium* or *Serratia marcesans* and various *Pseudomonas* species can all be used as hosts. In one specific embodiment, the prokaryotic host cell is enteropathogenic E. coli.

In addition, attenuated or non-pathogenic strains of bacteria may be useful in delivery of fusion polypeptides to the intestinal mucosa. For example, live attenuated (e.g., EspA or EspB deleted) strains containing a fusion protein or vector encoding a Tir fusion polypeptide may be used to deliver the fusion polypeptide to a host. In this manner the attenuated bacteria can provide the fusion protein to a host wherein the fusion protein is presented by the host cell in order to confer a specific immune response.

Among the eukaryotic organisms which may serve as host cells are yeast strains such as PS23-6A, W301-18A, LL20, D234-3, INVSC1, INVSC2, YJJ337. Promoter and enhancer sequences such as gal1 and pEFT-1 are useful. Vra-4 also provides a suitable enhancer sequence. Sequences useful as functional origins of replication include ars1 and 2µ circular plasmid.

As used herein, the terms "espA" "espB" and "eaeA" refer to genes other than tir that encode pathogenic E. coli-secreted proteins. As used herein, the term "EspA" "EspB" and "intimin" refer to the proteins encoded by the espA, espB and the eaeA genes, respectively. Intimin is the product of a bacterial chromosomal LEE locus, eaeA, and is a 94 kDa EPEC outer membrane protein that is needed for intimate adherence. EspA, EspB, and intimin are secreted by EHEC as well as by EPEC.

Antibodies and Immunological Methods.

The Tir polypeptides of the invention can also be used to produce antibodies which are immunoreactive or bind to epitopes of the Tir polypeptides. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., *Nature* 256: 495 (1975); *Current Protocols in Molecular Biology*, Ausubel, et al., ed., (1989)).

The term "antibody" as used in this invention includes intact molecules as well as fragments thereof, such as Fab, Fab', $F(ab')_2$, Fv, and single chain antibody that can bind the epitope. These antibody fragments retain some ability selectively to bind with its antigen or receptor.

Methods of making these fragments are known in the art. (See, for example, Harlow and Lane, *Antibodies: A Laboratory Manual*, Cold Spring Harbor Laboratory, New York (current edition), incorporated herein by reference). In EXAMPLE I, polyclonal mouse and rat antibodies to the 78 kDa EPEC protein were generated by such methods.

An epitope is any antigenic determinant on an antigen to which the paratope of an antibody binds. Epitopes usually consist of chemically active surface groupings of molecules such as amino acids or sugar side chains and usually have specific three dimensional structural characteristics, as well as specific charge characteristics.

If needed, polyclonal or monoclonal antibodies can be further purified, for example, by binding to and elution from a matrix to which the peptide or a peptide to which the antibodies are raised is bound. Those of skill in the art will know of various techniques common in the immunology arts for purification and/or concentration of polyclonal antibodies, as well as monoclonal antibodies (See, e.g., Coligan, et al., Unit 9, *Current Protocols in Immunology*, Wiley Interscience, current edition, incorporated by reference).

The invention also provides peptide epitopes for use in designing tir specific nucleotide probes or anti-Tir antibodies. Such probes or antibodies can be used to identify proteins or genes that may be involved in the virulence of other pathogens, including but not limited to polypeptides or polynucleotides from Gram-negative bacteria.

The antibodies of the invention, including polyclonal and monoclonal antibodies, chimeric antibodies, single chain antibodies and the like, have with the ability to bind with high immunospecificity to the Tir proteins, peptides or nucleotide sequences of the invention, or fragments thereof. These antibodies can be unlabeled or suitably labeled. Antibodies of the invention can be used for affinity purification of Tir for example. Antibodies of the invention may be employed in known immunological procedures for qualitative or quantitative detection of these proteins or peptides in cells, tissue samples, sample preparations or fluids. Antibodies of the invention may be employed in known immunological procedures for qualitative or quantitative detection of the nucleotide sequences or portions thereof.

The invention provides a method for detecting Tir polypeptide in a sample, including contacting a sample from a subject with an antibody to Tir polypeptide; and detecting binding of the antibody to Tir polypeptide. Binding is indicative of the presence of Tir polypeptide in the sample. As used herein, the term "sample" includes material derived from a mammalian or human subject or other animal. Such samples include but are not limited to hair, skin samples, tissue sample, cultured cells, cultured cell media, and biological fluids. For example, Tir polypeptide can be detected in HeLa cell (e.g., human) culture. In EXAMPLE II, Hp90 was detected in J774 macrophage-like cells by the use of such methods.

As used herein, the term "tissue" refers to a mass of connected cells (e.g., CNS tissue, neural tissue, or eye tissue) derived from a human or other animal and includes the connecting material and the liquid material in association with the cells. As used herein, the term "biological fluid" refers to liquid material derived from a human or other animal. Such biological fluids include but are not limited to blood, plasma, serum, serum derivatives, bile, phlegm, saliva, sweat, amniotic fluid, and cerebrospinal fluid (CSF), such as lumbar or ventricular CSF.

As used herein, the term "sample" also includes solutions containing the isolated polypeptide, media into which the polypeptide has been secreted, and media containing host cells which produce the Tir polypeptide. For example, a sample may be a protein samples which is to be resolved by SDS-PAGE and transferred to nitrocellulose for Western immunoblot analysis. The quantity of sample required to obtain a reaction may be determined by one skilled in the art by standard laboratory techniques. The optimal quantity of sample may be determined by serial dilution.

In one embodiment, the presence of Tir polypeptide in the sample is indicative of infection by enteropathogenic *E. coli*. In another embodiment, the presence of Tir polypeptide in the sample is indicative of infection by enterohemorrhagic *E. coli*.

Proteins, protein fragments, and synthetic peptides of the invention are projected to have numerous uses including prognostic, therapeutic, diagnostic or drug design applications. Proteins, protein fragments, and synthetic peptides of the invention will provide the basis for preparation of monoclonal and polyclonal antibodies specifically immunoreactive with the proteins of the invention. In one embodiment, the invention provides a method of immunizing a host susceptible to disease caused by Tir-producing *E. coli*, by administering to a host with the polypeptide of claim 1; and inducing a protective immune response in the host to Tir polypeptide. The infection of the host by Tir-producing organism is thereby prevented. In a more specific embodiment, the Tir-producing organism is an *E. coli* strain. In an even more specific embodiment, the *E. coli* strain is either enteropathogenic or enterohemorrhagic *E. coli*.

In another embodiment, the invention provides a method of ameliorating disease caused by Tir-producing organism, by immunizing a host with Tir polypeptide and inducing an immune response in the host to the Tir polypeptide. In a more specific embodiment, the Tir-producing organism is an *E coli* strain. In an even more specific embodiment, the *E. coli* strain is either enteropathogenic or enterohemorrhagic *E. coli*.

In one embodiment, the immunized host is human. Humans can be immunized by any of the standard protocols well-known to those in the medical art. Enteropathogenic *Escherichia coli* (EPEC) is a leading cause of infant diarrhea and was the first *E. coli* shown to cause gastroenteritis. EPEC continues to be a significant cause of infantile diarrhea in developing nations contributing to high morbidity and mortality. Using human volunteers, it has been shown that intimin is needed for full EPEC virulence (Donnenberg et al., *J. Clin. Inv.* 92: 1412–7 (1993)). Several animal models have documented the role of intimin in virulence. The intimate interactions that occur between EPEC secreted proteins and the host cell surface emphasize the complexity of host pathogen interactions, and provide valuable tools to exploit and study cellular function and bacterial disease, in addition to potential uses in therapeutics.

In another embodiment, the immunized host is bovine. Cattle can be immunized by any of the standard protocols well-known to those in the veterinary art. Cattle are vaccinated then with Tir, EspA, EspB, intimin, or combinations thereof. The adherence of EHEC to vaccinated cows is blocked by the bovine immune response. Vaccinated cattle therefore do not become EHEC carriers.

EHEC has been linked to many food-borne outbreaks and sporadic cases of hemorrhagic colitis and hemolytic uremic syndrome worldwide. The most common epidemiologically-associated food is ground beef. EHEC causes no disease symptoms in cattle, but beef and dairy cattle carry EHEC in their intestinal tracts. Contamination of carcasses occurs during slaughter operations. The use of vaccinated cattle is useful in reducing the occurrence of beef contaminated by enterohemorrhagic *E. coli*.

The invention provides a method for detecting tir polynucleotide in a sample, by contacting a sample suspected of containing tir polynucleotide with a nucleic acid probe that hybridizes to tir polynucleotide; and detecting hybridization of the probe with tir polynucleotide. The detection of hybridization is indicative of tir polynucleotide in the sample.

Recombinant Genetic Methods

The invention provides a recombinant method for producing tir polynucleotide, including inserting a nucleic acid encoding a selectable marker into the polynucleotide encoding Tir polypeptide. The resulting polynucleotide encodes a recombinant Tir polypeptide containing the selectable marker. As used herein, a "selectable marker" may be any genetic sequence other than a tir sequence which can be detected or which encodes an amino acid sequence which can be detected. For example, a selectable marker may be a herpes simplex virus (HSV) tag, for which there are commercially available antibodies. In EXAMPLE VI, two genetic fusions were constructed linking the sequence encoding either the T7 or HSV epitopes to the 5' or 3' of tir, respectively, by the use of such methods.

The invention provides a method of producing fusion proteins. Because Tir is a secreted protein, it is useful as a fusion partner for cloning and expressing other peptides and proteins. For example, Tir fused to a protein of interest is recombinantly produced in a host cell, e.g., *E. coli*, and the fusion protein is secreted into the culture media in which the transformed host is grown. The fusion protein can be isolated by anti-Tir antibodies followed by cleavage of Tir from the peptide or protein of interest. ELISA or other immunoaffinity methods can be used to identify the Tir fusion protein. The invention provides a method of producing a Tir fusion protein including growing a host cell containing a polynucleotide encoding Tir operably linked to a polynucleotide encoding a polypeptide or peptide of interest under conditions which allow expression and secretion of the fusion polypeptides and isolating the fusion polypeptide. The term "operably linked or associated" refers to functional linkage between a promoter sequence and the structural gene or genes in the case of a fusion protein, regulated by the promoter nucleic acid sequence. The operably linked promoter controls the expression of the polypeptide encoded by the structural gene (e.g., the fusion protein).

Preferred organisms in which to practice the recombinant methods of invention include but are not limited to bacteria. In another embodiment, the organism which is used to generate a mutation in a polynucleotide encoding Tir polypeptide is *E. coli*. Among the *E. coli* that may be transformed are enteropathogenic and enterohemorrhagic *E. coli*.

The invention provides a recombinant method for producing Tir polypeptide, by growing a host cell containing a polynucleotide encoding Tir polypeptide under conditions which allow expression and secretion of Tir polypeptide; and isolating the polypeptide. Methods of producing polypeptides and peptides recombinantly are within the scope of this invention. As used herein, the term "conditions which allow expression and secretion" refers to suitable conditions such that the nucleic acid is transcribed and translated and isolating the polypeptide so produced. The polypeptide produced may be a protein secreted into the media. Media includes a fluid, substance or organism where microbial growth can occur or where microbes can exist. Such environments can be, for example, animal tissue or bodily fluids, water and other liquids, food, food products or food extracts, and certain inanimate objects. For example, microbes may grow in Luria-Bertani (LB) media. It is not necessary that the environment promote the growth of the microbe, only that it permits its subsistence.

Agents that Interfere with Binding Between Tir and Intimin

In another embodiment, the present invention relates to agents that interfere with binding between Tir and intimin. Such binding agents may interfere by competitive inhibition, by non-competitive inhibition or by uncompetitive inhibition. Interference with normal binding between Tir and intimin can result in a useful pharmacological effect.

In another embodiment, the invention provides a method for identifying a composition which binds to Tir. The method includes incubating components comprising the composition and Tir under conditions sufficient to allow the components to interact and measuring the binding of the composition to Tir. Compositions that bind to Tir include peptides, peptidomimetics, polypeptides, chemical compounds and biologic agents.

Incubating includes conditions which allow contact between the test composition and Tir. Contacting includes in solution and in solid phase. The test ligand/composition may optionally be a combinatorial library for screening a plurality of compositions. Compositions identified in the method of the invention can be further evaluated, detected, cloned, sequenced, and the like, either in solution or after binding to a solid support, by any method usually applied to the detection of a specific DNA sequence such as PCR, oligomer restriction (Saiki et al., *Bio/Technology* 3: 1008–1012 (1985)), allele-specific oligonucleotide probe analysis (Conner et al., *Proc. Natl. Acad. Sci. USA* 80: 278 (1983)), oligonucleotide ligation assays (OLAs) (Landegren et al., *Science* 241: 1077 (1988)), and the like. Molecular techniques for DNA analysis have been reviewed by Landegren et al., *Science* 242: 229–237 (1988).

To determine if a composition can functionally complex with the receptor protein, induction of the exogenous gene is monitored by monitoring changes in the protein levels of the protein encoded for by the exogenous gene, for example. When a composition is found that can induce transcription of the exogenous gene, it is concluded that this composition can bind to the receptor protein coded for by the nucleic acid encoding the initial sample test composition.

Expression of the exogenous gene can be monitored by a functional assay or assay for a protein product, for example. The exogenous gene is therefore a gene which will provide an assayable/measurable expression product in order to allow detection of expression of the exogenous gene. Such exogenous genes include, but are not limited to, reporter genes such as chloramphenicol acetyltransferase gene, an alkaline phosphatase gene, beta-galactosidase, a luciferase gene, a green fluorescent protein gene, guanine xanthine phosphoribosyltransferase, alkaline phosphatase, and antibiotic resistance genes (e.g., neomycin phosphotransferase).

Expression of the exogenous gene is indicative of composition-receptor binding, thus, the binding or blocking composition can be identified and isolated. The compositions of the present invention can be extracted and purified from the culture media or a cell by using known protein purification techniques commonly employed, such as extraction, precipitation, ion exchange chromatography, affinity chromatography, gel filtration and the like. Compositions can be isolated by affinity chromatography using the modified receptor protein extracellular domain bound to a column matrix or by heparin chromatography.

Also included in the screening method of the invention is combinatorial chemistry methods for identifying chemical compounds that bind to Tir. Thus, the screening method is also useful for identifying variants, binding or blocking agents, etc., which functionally, if not physically (e.g., stearically) act as antagonists or agonists, as desired.

The invention provides a method for identifying a compound which interferes with the binding of a Tir polypeptide to intimin. The binding of Tir polypeptide to intimin is measured under standard conditions well-known to those in the biochemical arts. The binding affinity of Tir polypeptide to intimin is determined. Then, a candidate compound suspected of interfering with the binding of Tir polypeptide to intimin is added to a mixture or solution of Tir polypeptide and intimin. The binding of Tir polypeptide to intimin is then measured under the standard conditions. The binding affinity of Tir polypeptide to intimin in the presence of the compound is determined. The assay compares the binding of the Tir polypeptide to intimin in the presence of the compound to the binding of the Tir polypeptide in the absence of the compound. Compounds that interfere with the binding of Tir polypeptide to intimin are useful in the treatment of pathogens where the binding of Tir polypeptide to intimin is involved in pathogenesis, including such pathogens as EPEC and EHEC. Furthermore, the polypeptide or nucleotide sequences of the invention can be used to identify compounds or compositions which interact (e.g., bind) with them and affect their biological activity. Such effects include inhibition or stimulation of Tir activity or secretion.

The invention provides a method for using the Tir-intimin system for cell delivery. As used herein, a "cell delivery vehicle" is a compound, capable of containing a second compound of interest, that can be absorbed by a cell. In one embodiment, cells are infected with an intimin mutant, thereby delivering Tir to the infected cells. In a more specific embodiment, the cells are in vivo. In another specific embodiment, the cells are in vitro. In an alternative embodiment, the attaching and effacing pathogen is an intimin mutant. Intimin (eaeA) mutants have been described by Kenny and Finlay, *Infection & Immunity* 65(7) 2528–2536 (1997). In another alternative embodiment, Tir is expressed in a cell by recombinant genetic methods described supra.

Molecules of interest can be targeted to Tir-containing cells by using an intimin-containing cell delivery vehicle. As used herein, "Tir-containing cells" are cells which contain Tir. For example, epithelial cells may contain Hp90. As used herein, an "intimin-containing cell delivery vehicle" includes a cell delivery vehicle which comprises intimin or an intimin fragment capable of binding to Tir on the surface of the delivery vehicle. In one embodiment, the intimin-containing cell delivery vehicle is a bead.

In another embodiment, the intimin-containing cell delivery vehicle is a liposome. Liposomes may be modified using methods well known in the art by attaching thereto, either directly, or indirectly, such as by means of target-specific ligands, such as intimin, in order to impart organ or cell target specificity, as described by Malone et al., *Proc. Nat'l. Acad. Sci, U.S.A.*, 86:6077, (1989) and Gregoriadis, *Immunology Today*, 11(3):89 (1990).

Various biologically active substances can be incorporated by encapsulation within the liposomes. These substances include drugs, as well as other kinds of pharmaceutical materials such as DNA, RNA, proteins of various types, protein hormones such as insulin, growth factors, cytokines, monokines, lymphokines, and proteins and carbohydrates that serve as immunogens for vaccination.

Biologically active substances effective for cosmetic uses can also be incorporated by encapsulation into liposomes. These include moisturizers, vitamins, enzymes, and perfumes. In addition, herbicides, pesticides, fungicides etc. are examples of biologically active substances with agricultural uses that can be encapsulated into liposomes.

The dosage range appropriate for in vivo use in humans of the biologically active substance in liposomes of this invention includes the range of 0.001–6,000 body surface area. While doses outside the foregoing dose range may be given, this range encompasses the breadth of use for practically all the biologically active substances. However, for a particular therapeutic agent the preferred concentration can be easily ascertained as previously described.

The intimin-containing cell delivery vehicle may be administered by any desired route; for example, intratumoral, intra-articular (into joints), intramuscular, intrathecal, intraperitoneal, subcutaneous, intravenous, intralymphatic, oral and submucosal.

The invention provides a method for detecting cytoskeleton of a cell, by contacting a cell cytoskeleton with Tir polypeptide; and detecting the binding of Tir polypeptide to cell cytoskeleton. As used herein, the term "cytoskeleton" refers to a network of molecular filaments (such as actin, microtubules, etc.) that provide a structure for the cytoplasm of a eukaryotic cell. The A/E lesion (or pedestal) is associated with the assembly of highly organized cytoskeletal structures in epithelial cells immediately beneath the adherent bacteria that include the cytoskeletal components actin, α-actinin, myosin light chain, ezrin, and talin. Tir binds to cytoskeleton. Detection of Tir polypeptide binding to cytoskeleton may be accomplished by several methods. In one embodiment, Tir binding is detected by subsequent binding to Tir by anti-Tir antibodies. Examples of this embodiment are provided in EXAMPLE I. In another embodiment, Tir binding to cytoskeleton is detected by subsequent binding to Tir by intimin. Examples of this embodiment are provided in EXAMPLE VII. In yet another embodiment, the Tir polypeptide which binds to cytoskeleton is a fusion protein.

Kits

This invention includes a kit containing one or more antibodies of the invention as well as a nucleotide based kit. In one embodiment, the kit is useful for the detection of Tir polypeptide and is a carrier means compartmentalized to receive in close confinement a container containing an antibody which binds to Tir polypeptide. As used herein, a "container means" includes vials, tubes, and the like, each of the container means comprising one of the separate elements to be used in the method.

In one embodiment, the antibody which binds to Tir polypeptide is detectably labeled. In a more specific embodiment, the label is selected from the group consisting of radioisotope, a bioluminescent compound, a chemiluminescent compound, a fluorescent compound, a metal chelate, and an enzyme.

In another embodiment, the kit is useful for the detection of a tir polynucleotide and is a carrier means compartmentalized to receive in close confinement a container containing the nucleic acid probe that hybridizes to tir polynucleotide. In one embodiment, nucleic acid probe that hybridizes to tir polynucleotide is detectably labeled. In a more specific embodiment, the label is selected from the group consisting of radioisotope, a bioluminescent compound, a chemiluminescent compound, a fluorescent compound, a metal chelate, and an enzyme.

In another embodiment, the kit is useful for the detection of a tir polynucleotide and is a carrier means compartmentalized to receive in close confinement a container containing a first container containing a first nucleic acid probe that hybridizes to one of two strands of tir polynucleotide, and a second container containing a second nucleic acid probe that hybridizes to the other of two strands of tir polynucleotide. The kit may be used for amplifying a tir polynucleotide sequence, for example, by PCR methods. In a specific embodiment, the first primer is complementary to one of two strands at one end of the tir sequence to be amplified and the second primer is complementary to the other of two e strands at the other end of the tir polynucleotide. Because the newly synthesized DNA strands can subsequently serve as additional templates for the same primer sequences, successive rounds of primer annealing, strand elongation, and dissociation produce rapid and highly specific amplification of the desired sequence.

The following examples are intended to illustrate but not limit the invention. While they are typical of those that might be used, other procedures known to those skilled in the art may alternatively be utilized.

EXAMPLE I

Antibodies to a 78 kDa EPEC-Secreted Protein Cross-React with Hp90

The purpose of this EXAMPLE is to show that antibodies to a 78 kDa EPEC-secreted protein cross-react with Hp90. During the attempts to purify Hp90, it was discovered that a polyclonal rabbit antiserum raised against EPEC recognized a protein that co-migrated precisely with enriched Hp90 from mammalian cell membranes. This cross-reactive band was not present when HeLa cells were infected with mutants defective for type III secretion, which also do not cause Hp90 tyrosine phosphorylation. Following infections which used radiolabeling conditions that specifically label EPEC but not HeLa proteins, anti-phosphotyrosine (PY) antibodies immunoprecipitated a radiolabeled protein that co-migrated with Hp90. In contrast, no radiolabeled Hp90 was precipitated when HeLa cell proteins were labeled. These preliminary findings suggested that hypothesis that Hp90 might be of bacterial origin.

If Hp90 was of bacterial origin, EPEC should be able to secrete this protein. EPEC secretes several proteins that are involved in activating host cell signals and other events needed for intimate binding. EPEC does not appear to secrete any visible protein of 90 kDa, the molecular mass of Hp90. The secretion of EPEC proteins was optimized so that, under special culture conditions, EPEC secretes two additional proteins of 72 and 78 kDa, in addition to EspA (25 kDa), EspB (37 kDa), EspC (110 kDa), and two other proteins of 39 and 40 kDa. The culture conditions are described in Kenny and Finlay, *Proc. Natl. Acad. Sci. USA* 92: 7991–5 (1995). The 72 and 78 kDa bands had the same amino terminal sequence, (PIGNLGNNVNGNHLIPPAP-PLPSQTDGAAR; SEQ ID NO:7), which was unrelated to any known EPEC protein. The amino terminal sequence was determined as follows: Proteins were transferred to PVDF paper, visualized with Ponceau red and excised for analysis.

Additionally, antibodies raised against the other EPEC secreted proteins did not recognize these proteins. Higher levels of the secreted 72 and 78 kDa proteins occurred when multiple copies of the Per positive regulon and special growth conditions were used. High levels of EPEC protein secretion were obtained by diluting LB grown EPEC/CVD450 1:50 in M9 minimal media containing 44 mM $NaHCO_3$, and growing for 7 hr. The plasmid pCVD450 encoding the Per regulon was maintained using tetracycline (25 μg/ml final concentration). Bacteria were grown overnight in LB broth at 37° C. without shaking prior to infection. Supernatants were concentrated by the addition of trichloroacetic acid (10% vol/vol). Polyclonal mouse and rat antibodies to the 78 kDa EPEC protein were generated, to determine if these antibodies could recognize Hp90.

Polyclonal mouse and rat antibodies to the 78 kDa EPEC protein were generated as follows: High levels of EPEC protein secretion were induced as above and supernatants concentrated by the addition of 40% ammonium sulfate (wt/vol) overnight. After centrifugation the resulting pellet was resuspended in phosphate-buffered saline (PBS) plus phenylmethylsulfonyl fluoride (PMSF, 0.1 mM final conc.) and dialyzed against PBS. The concentrated proteins were resuspended in loading buffer and resolved by SDS-12% PAGE. After transferring to nitrocellulose the proteins were visualized by Ponceau red, excised, fragmented by sonication, and used to immunize mice and rats. The titer was assessed by immunoblot analysis against EPEC/CVD450 secreted proteins. Antisera was used at 1:2,000–1:5,000 in immunoblot analysis, and at 1:100–1:200 for immunofluorescence microscopy. EPEC-infected HeLa cells were fractionated according to the method of Kenny and Finlay, *Infection & Immunity* 65 (1997), using saponin to release cytoplasmic proteins and Triton® X-100 to solubilize membrane proteins and these factions were probed with both anti-PY (to detect Hp90) and anti-EPEC 78 kDa protein antibodies. HeLa (CCL 2, ATCC) cells were cultured in Dulbecco's Modified Eagles Media containing 10% fetal calf serum.

Figure 1B:
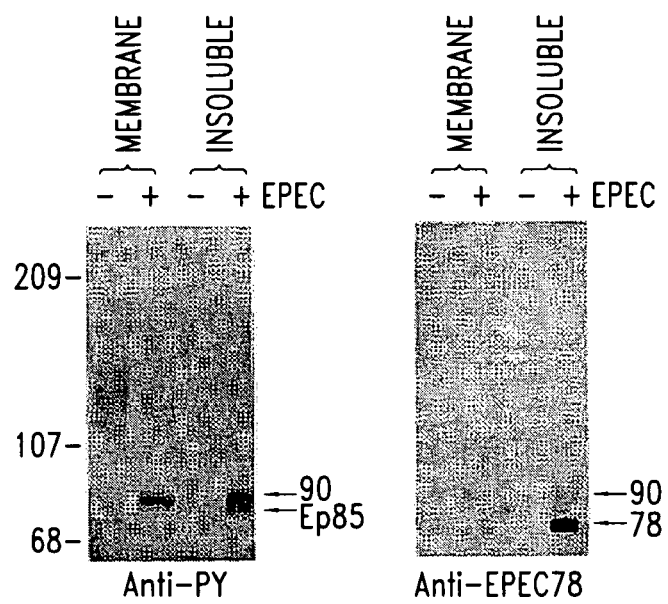
FIG. 1B shows a Western analysis. Membrane and insoluble fractions from uninfected or EPEC infected HeLa cells were loaded in duplicate and resolved by SDS-6% PAGE. After blotting to nitrocellulose the samples were probed with anti-PY (PY) or anti-EPEC 78 kDa antibodies. Molecular mass markers are in kDa. Ep85 is the 85 kDa tyrosine phosphorylated EPEC protein. (−) indicates uninfected cells and (+) indicates EPEC infected HeLa cells.

Both antibodies reacted with proteins that behaved as Hp90 within the mammalian cell membrane fraction from infected but not uninfected cells (FIG. 1B). Both antibodies also reacted with a 90 kDa protein in the insoluble (bacteria and cytoskeleton) fraction, which represents Hp90 bound to bacteria. In addition, anti-PY antibodies recognized Ep85, an 85 kDa tyrosine phosphorylated EPEC protein, in the insoluble fraction. The anti-EPEC 78 kDa antibodies, but not the anti-PY antibodies, also reacted with the bacterial form of the 78 kDa protein in the insoluble bacterial containing fraction.

Therefore, antibodies to a 78 kDa EPEC-secreted protein cross-react with Hp90, evidencing that Hp90 is an EPEC-secreted protein.

EXAMPLE II

Hp90 is the Tyrosine Phosphorylated Form of the 78 kDa EPEC-Secreted Protein

The purpose of the immunoprecipitation experiments in this EXAMPLE was to show that Hp90 is the tyrosine phosphorylated form of the 78 kDa EPEC-secreted protein.

Figure 2A:
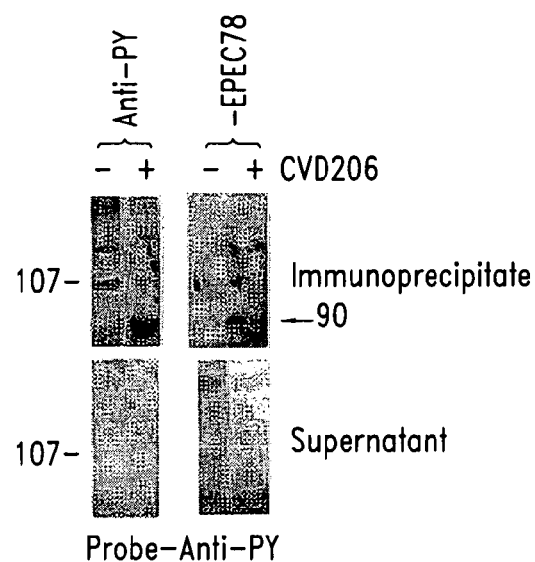
FIG. 2A shows immunoprecipitation results. The membrane fraction from uninfected or intimin mutant infected J774 cells was isolated, aliquotted into two, and then immunoprecipitated with anti-PY or anti-EPEC 78 kDa antibodies. The resulting immunoprecipitates and cleared supernatants were resolved by SDS-6% PAGE. After blotting to nitrocellulose the samples were probed with anti-PY. (−) indicates uninfected cells and (+) indicates CVD206 infected J774 cells.

Because high levels of Hp90 are detected in J774 macrophage-like cells (TIB 67, ATCC), J774 cells were infected with the intimin mutant, CVD206, to maximize membrane levels of Hp90, fractionated, and the Triton® X-100 soluble membrane fraction innumoprecipitated with either anti-PY or anti-EPEC 78 kDa antibodies. J774 A.1 cells were cultured in Dulbecco's Modified Eagles Media containing 10% fetal calf serum. Immunoprecipitation was carried out as described by Kenny and Finlay, *Infection & Immunity* 65 (1997). The immunoprecipitates and post-immunoprecipitate supernatants were then resolved by SDS-PAGE, transferred to nitrocellulose, and probed with anti-PY antibodies (FIG. 2A). Using this procedure, Hp90 was cleared from the membrane fraction of infected cells with both antibodies (supernatant in FIG. 2A) and a co-migrating 90 kDa protein was recognized in the immunoprecipitate with both antibodies.

Figure 2B:
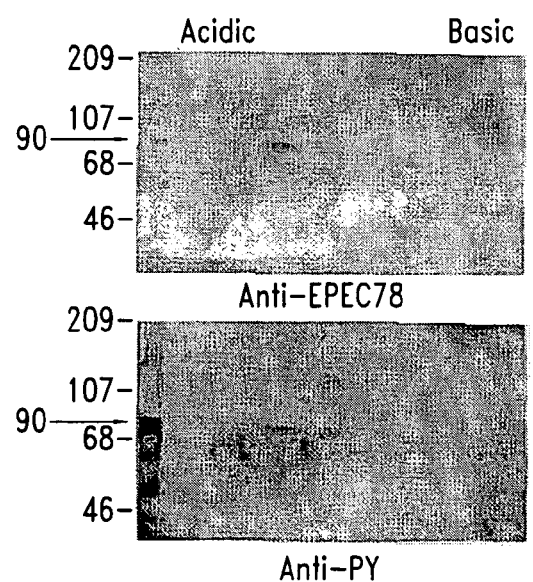
FIG. 2B shows a two dimensional gel electrophoresis of intimin mutant infected J774 cell membrane fractions probed with anti-PY or EPEC 78 kDa antibodies. The membrane fraction from intimin mutant infected J774 cells was prepared as described, and resolved by isoelectric focusing followed by SDS-8%-PAGE, prior to transfer to nitrocellulose for immunoblotting with anti-PY or anti-EPEC 78 kDa antibodies.

Additional evidence that both antibodies were recognizing the same protein was obtained by performing two dimensional gel electrophoresis. Two dimensional gel electrophoresis was performed as follows: Triton® X-100 soluble membrane fractions from J774 cells were prepared as described by Rosenshine et al., *EMBO J.* 15:2613–2624 (1996). The membranes were further purified by heating at 90° C. for 5 min followed by ultracentrifugation at 50,000× g, 30 min, 4° C. 100 μl solubilized membrane protein was precipitated using $CHCl_3$/acetone/$H_2O$, resuspended in 12.5 μl 2D gel sample buffer, and resolved on first-dimension isoelectric focusing gels, using 4% (w/v) polyacrylamide mini-isoelectric focusing gels (BioRad) containing 2% ampholines (0.4% pH 3–10, 1.6% pH 5–7) at 700 V, 3.5 hrs. Second dimension electrophoresis was performed on 8% SDS-polyacrylamide gels. The proteins were transferred to nitrocellulose for immunoblotting with the appropriate antisera. Membranes containing Hp90 were isolated from CVD206 infected J774, and proteins separated by isoelectric focusing followed by SDS-PAGE. Duplicate samples were transferred to nitrocellulose and probed with either anti-PY or anti-EPEC 78 kDa antibodies (FIG. 2B).

Probing with the anti-EPEC 78 kDa and anti-PY antibodies revealed that Hp90 actually consisted of several related proteins of similar molecular weight, but varying isoelectric points. After the blots were stripped and reprobed with the other antibody, they showed the same pattern of spots, indicating that Hp90 and the 78 kDa EPEC secreted proteins were the same protein. Based on these results and the fact that tyrosine phosphorylated Hp90 is the intimin receptor, this protein was named Tir, for translocated intimin receptor.

Figure 3:
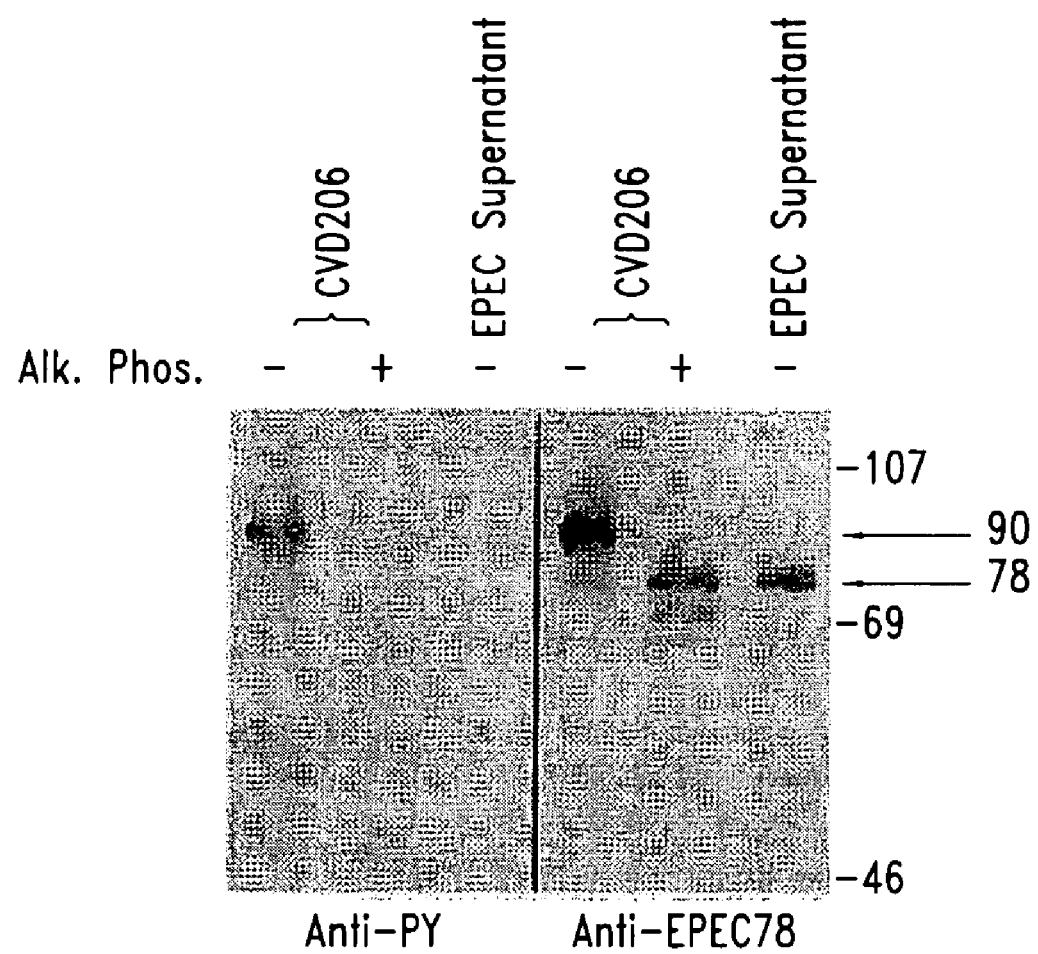
FIG. 3 shows that the migrational difference between secreted EPEC 78 and membrane associated Hp90 (Tir) is due to phosphorylation. HeLa cells were infected with the intimin mutant, CVD206, to induce Hp90 phosphorylation. Membrane fractions used for phosphatase treatment were isolated in the absence of phosphatase inhibitors, and incubated with 2 units of alkaline phosphatase for 4 hr at 37° C. Alkaline phosphatase treated (+) or untreated (−) samples as well as EPEC supernatant containing the secreted proteins were loaded in duplicate and resolved by SDS-6% PAGE. After blotting to nitrocellulose the samples were probed with anti-PY or anti-EPEC 78 kDa antibodies. Molecular mass markers are in kDa.

Tir in host cell membranes has a significantly different predicated molecular mass than the protein secreted from bacteria (90 kDa versus 78 kDa on SDS-PAGE). The difference was due to tyrosine phosphorylation of the 78 kDa protein in the host cell, which is not recognized by the PY antibodies in its bacterial secreted 78 kDa form (FIG. 3). To show this, membrane extracts prepared from the intimin mutant CVD206 infected HeLa cells were treated with alkaline phosphatase, which should remove all phosphate groups. An immunoblot was performed with the treated sample, probing with anti-EPEC 78 kDa and anti-PY antibodies. Cellular fractionation and alkaline phosphatase treatment was carried out as described by Kenny and Finlay, *Infection & Immunity* 65 (1997). Briefly, cultured HeLa cells were infected with EPEC, washed, and treated with 0.2% saponin to release the soluble cytoplasmic fraction in the presence of phosphatase and protease inhibitors. One percent Triton® X-100 was used to solubilize the membrane proteins from the remaining insoluble fraction which contains adherent bacteria, host nuclei and cytoskeleton. For alkaline phosphatase treatment, membrane fractions were isolated in the absence of phosphatase inhibitors, and incubated with 2 U of alkaline phosphatase (NEB) for 4 hr at 37° C.

As shown in FIG. 3, anti-PY antibodies recognized only the phosphorylated (90 kDa) form of Tir in untreated membranes. In contrast, the EPEC 78 antibodies recognize the 90 kDa Tir in untreated membranes and also a band of the same molecular mass as the secreted EPEC 78 kDa protein in the phosphatase treated membrane fractions. A lower molecular weight band was also detected which may be a breakdown product due to extended digestion. Alkaline phosphatase treatment of the EPEC 78 kDa secreted protein did not affect its migration.

These results indicate that Hp90 and the 78 kDa EPEC secreted proteins were the same protein. The difference in molecular masses between these two forms of Tir is due to an alkaline phosphatase-sensitive modification, presumably tyrosine and possibly serine or threonine phosphorylation.

EXAMPLE III

Anti-EPEC 78 kda Antibodies Colocalize with Hp90 in Mammalian Cells

The purpose of this EXAMPLE was to show that anti-EPEC 78 kDa antibodies colocalize with Hp90 in mammalian cells. Because antibodies against both PY and EPEC 78 kDa proteins recognized the same protein, it was examined whether they labeled infected HeLa cells similarly using immunofluorescence microscopy.

Figure 4A:
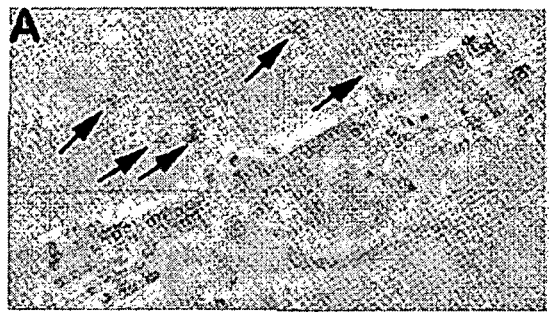
FIG. 4 shows that anti-PY and EPEC 78 kDa antibodies label identical structures in infected mammalian cells. Immunofluorescent labeling of HeLa cells following 3 hr EPEC infection. Fixed and permeabilized cells were co-labeled with either anti-PY and anti-EPEC 78 kDa antibodies (FIGS. 4A–4D), or FITC-phalloidin and anti-EPEC 78 kDa (FIGS. 4E–4H). Panels
FIG. 4D and FIG. 4H are superimpositions of panels FIG. 4B and FIG. 4C, and FIG. 4F and FIG. 4G, respectively. For panels FIG. 4E–FIG. 4H, fields were selected to show infected cells with most developed actin pedestals. Arrows indicate nonadherent bacteria.
Figure 4E:
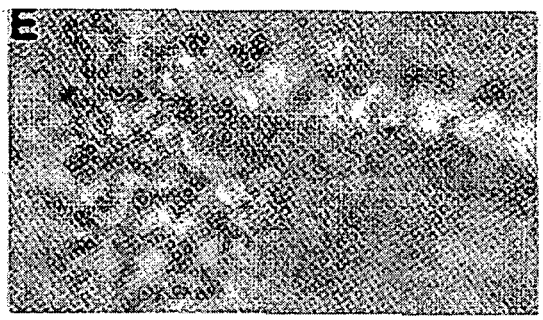
Figure 4B:
Figure 4F:
Figure 4C:
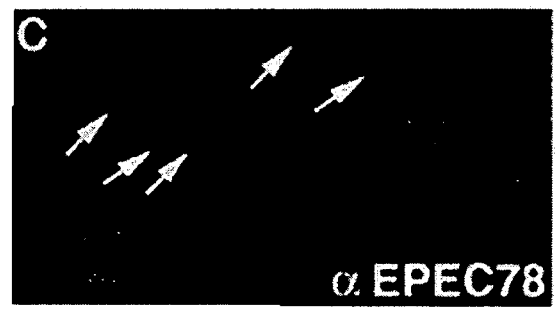
Figure 4G:
Figure 4D:
Figure 4H:

Tyrosine phosphorylated proteins, presumably Hp90 (i.e. tyrosine phosphorylated Tir), are apparent in distinct horseshoe shaped structures at the tip of actin-rich pedestals beneath adherent bacteria. PY antibodies only recognize this protein if infected HeLa cells are permeabilized, indicating that PY residues are not exposed on the cell surface. When infected HeLa cells were co-labeled with antibodies against PY (FIG. 4B) and the EPEC 78 kDa protein (FIG. 4C), the labeling pattern was completely superimposable (FIG. 4D). Anti-EPEC 78 kDa antibodies only stained areas of the HeLa cells immediately beneath the bacteria, and did not label free bacteria (see arrows in FIG. 4C). When infected HeLa cells were labeled with both anti-EPEC 78 kDa and FITC-phalloidin to stain actin (FIGS. 4E–H), anti-EPEC 78 kDa staining was localized to the tip of the actin pedestal, directly underneath bacteria, rather than staining the entire actin pedestal (FIG. 4H). This pattern of staining is identical to that observed by co-labeling with anti-PY and FITC-phalloidin.

These results also show that Tir is phosphorylated in the host cell.

EXAMPLE IV

Figure 5:
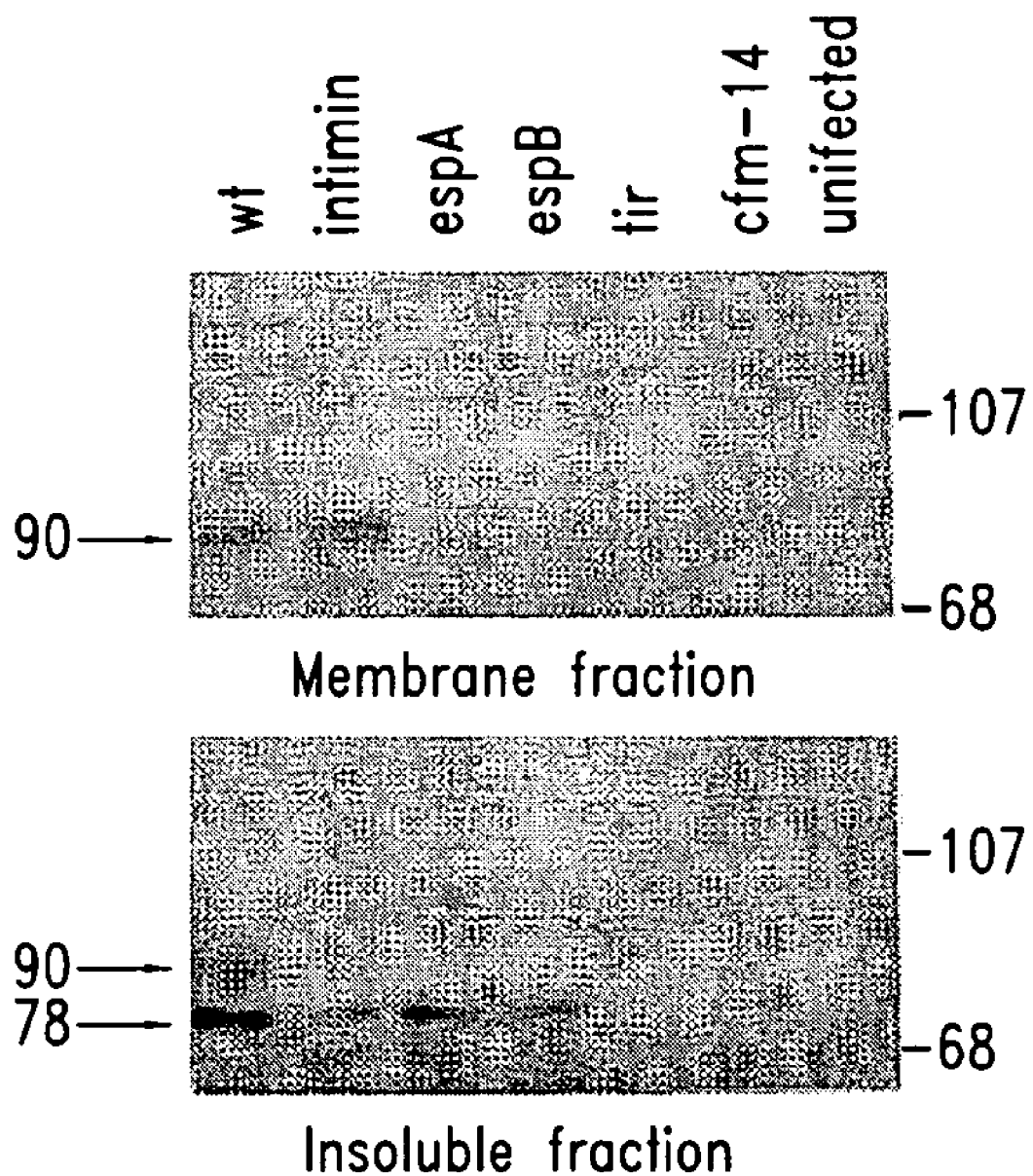
FIG. 5 shows that the transfer of Tir to host cells is dependent on the type III secretion apparatus and the EPEC secreted proteins EspA and EspB. HeLa cells were infected with EPEC or strains containing mutations in eaeA (intimin), espA, tir, or cfm-14 and their Triton® X-100 soluble (membrane) and insoluble (bacteria and cytoskeleton) fractions isolated. Samples were resolved by SDS-6% PAGE and transferred to nitrocellulose prior to probing with anti-EPEC 78 kDa antibodies. Tir related proteins (90, 78 kDa) are indicated by arrows. Molecular mass markers are in kDa.

The Type III Secretion Apparatus and its Secreted Proteins, EspA and EspB, Facilitate Delivery of Tir into Host Cells The purpose of this EXAMPLE was to examine the role of the type III secretion apparatus and its secreted proteins on Tir delivery into HeLa cells. Strains containing mutations in genes encoding the type III secretion apparatus (sep and cfm) or secreted proteins, EspA or EspB (espA or espB), do not produce a tyrosine-phosphorylated Tir in host cells. However, the non-tyrosine phosphorylated form of Tir might still be delivered to the host cell. Membrane extracts from EPEC or mutant infected HeLa cells were isolated and probed with anti-PY and anti-EPEC 78 kDa antibodies (FIG. 5).

The tyrosine phosphorylated 90 kDa form of Tir was only detected with anti-PY antibodies in the EPEC and CVD206 infected membranes. The anti-EPEC 78 kDa antibodies recognized the same 90 kDa band in EPEC and CVD206 membrane extracts, but strains containing mutations in espA, espB, or cfm-14 did not contain detectable levels of Tir in the membrane (FIG. 4) or cytoplasmic fractions. The 78 kDa form of Tir in EPEC or CVD206 infected cells was not detected, suggesting a rapid modification to 90 kDa. The bacterial form of the 78 kDa Tir protein was present in the insoluble fraction containing adherent bacteria of all these strains. Only the EPEC infected HeLa cell insoluble fraction contained the 90 kDa form of Tir which localizes to this fraction due to its interaction with intimin.

Therefore, EspA and EspB, which are both secreted by the type III system, are needed for efficient delivery of Tir to the host membrane fraction.

EXAMPLE V

Genetic Characterization and Mutation of the Gene Encoding Tir

The purpose of this EXAMPLE was to undertake a genetic characterization of the bacterial gene that encodes Tir. The amino terminal sequence of the 78 kDa EPEC protein was used to design a synthetic oligonucleotide, using the Locus of Enterocyte Effacement (LEE) codon usage preferences, to identify the homologous DNA sequence. DNA fragments overlapping the LEE region were examined, because this region is capable of eliciting Tir tyrosine phosphorylation when cloned and expressed in non-pathogenic *E. coli*.

The synthetic oligonucleotide hybridized to a single DNA fragment in the LEE region upstream of the intimin gene eaeA, which was then cloned and sequenced (FIG. 6A). The cloning and DNA sequence analysis of tir were performed as follows: Based on N-terminal protein sequence data of Tir, a degenerate oligonucleotide was designed and used this oligonucleotide in Southern hybridization under stringent conditions to identify and then clone a 3800 bp EcoRI fragment from the LEE region into the vector Bluescript SK(+) pSK-tir. The resulting vector was digested with Exonuclease III (Erase-a Base; Promega) to obtain a set of nested deletions, which were used to determine the DNA sequence of tir using the Taq DyeDeoxy™ Terminator Cycle Sequencing Kit from Applied Biosystems. Priming of DNA sequencing reactions utilized the M13 Forward Primer and the T3 Primer. EPEC strains E2348/69, CVD206, cfm 14-2-1(1), and, UMD872 (espA), UMD864 (espB) have been described by Donnenberg et al., *Infection & Immunity* 60: 3953–61(1990); Donnenberg et al., *Trends Microbiol.* 5: 109–114 (1993); Foubister et al., *Infection & Immunity* 62: 3038–40 (1994); Foubister et al., *J. Exp. Med* 179: 993–8 (1994); Jerse et al., *Proc. Natl. Acad. Sci. USA* 87, 7839–43 (1990); Kenny and Finlay, *Proc. Natl. Acad. Sci. USA* 92: 7991–5 (1995); and Rosenshine et al., *EMBO J.* 11: 3551–60 (1992)

The tir gene (SEQ ID NO:1; Genbank accession number AF013122) is located upstream of eaeA, with a previously described open reading frame, orfU, between eaeA and tir (FIG. 6B). Partial open reading frames containing homologies to orfU and the C-terminus of Tir are present in EPEC and the other attaching and effacing pathogens EHEC, RDEC and *Citrobacter rodentium* (formerly *C. freundii* biotype 4280) (Genbank accession numbers M58154, U32312, U60002, L11691). The amino terminal sequence of the purified protein matched exactly the predicted protein sequence, except that the amino terminal methionine was not present in the secreted EPEC protein. Proteins that are secreted by type III secretion systems retain their amino-terminal methionine residues. Because Tir lacks this methionine, Tir may not directly use the type III secretion system for its secretion, although its efficient transfer to host cells is dependent on EspA, EspB and the type III secretion pathway (FIG. 5).

Neither the tir gene nor its product, Tir, showed significant homology with any known genes or proteins using a BLAST homology search.

Although the Tir protein is predicted to encode a 56.8 kDa protein, a molecular mass of about 78 kDa was observed for the secreted protein, which may reflect some additional bacterial modification or abnormal migration due to amino acid composition or structural features. Tir contains two predicted membrane spanning sequences with six tyrosine residues in the C-terminal half of the protein which may serve as substrates for phosphorylation (FIG. 6A–6B). Tir is predicted to have two transmembrane domains (TM predict, ISREC, Switzerland) with the six tyrosine residues, potential kinase substrates, in the C-terminal half. As predicted for EspA and EspB, Tir appears to be slightly acidic (predicted pI of 5.16) which was verified by two dimensional gel electrophoresis analysis.

Figure 6C:
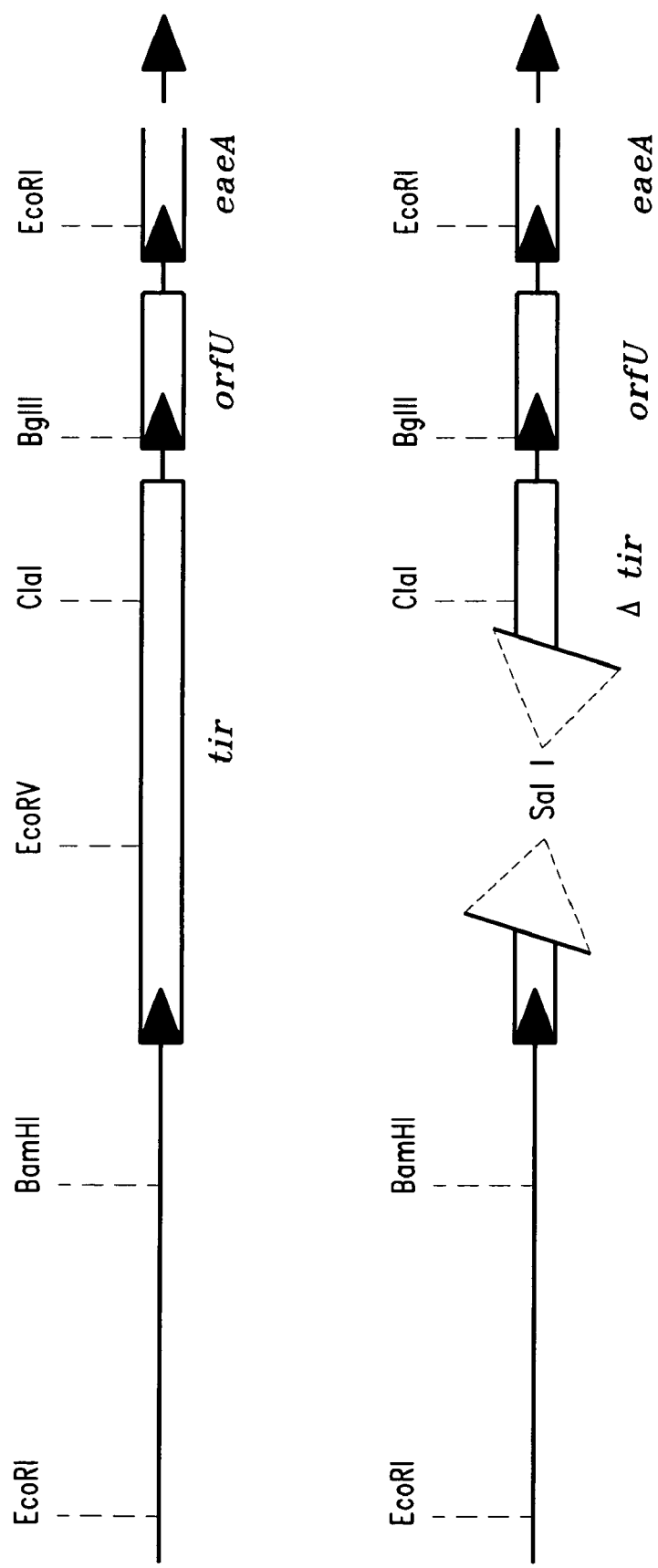
FIGS. 6A–B shows the nucleotide sequence (SEQ ID NO:13) and predicted protein (SEQ ID NO:14) of tir (A) and genetic map (C).

To show the role of this protein in pedestal formation a chromosomal deletion in the tir gene was constructed (FIG. 6C). The chromosomal deletion mutant was constructed as follows: the primers MS102+(5'-AAAGTCGACAAGAAC-CTGAGAACCAG-3'; SEQ ID NO:8) and MS103-(5'-TTTGTCGACTTATGTTTGTGAAGGTAGTGG3'; SEQ ID NO:9) were used to create a 5' deletion of 795 bp between bp 149 and bp 795 of the tir gene using inverse PCR amplification of pSK-tir. The oligonucleotide MS103 also introduced a SalI restriction site into the PCR product and a stop codon to terminate protein translation. The resulting 3000 bp SalI/SacI tir deletion fragment was cloned into the positive-selection suicide vector pCVD442 (Sal/SacI) and used to construct the deletion mutant by allelic exchange.

The resulting mutant strain did not express the EPEC 78 kDa protein or transfer Tir to HeLa cells (FIG. 5). In addition, this mutant did not cause significant accumulation of phosphotyrosine proteins or actin beneath adherent bacteria (FIG. 7A), although some actin was clustered in the vicinity of adherent bacteria similar to that seen with intimin mutants. The deletion mutation did not affect the secretion of the other EPEC secreted proteins or prevent the expression of intimin. When unpermeabilized HeLa cells were stained with anti-EPEC 78 kDa antibody, there was labeling of HeLa cell surfaces infected with the intimin mutant (which doesn't sequester Tir beneath bacteria), but no staining was observed with uninfected cells or those infected with the tir mutant, indicating that Tir epitopes are exposed on surface of infected HeLa cells.

These results show that Tir is a novel protein and tir is a novel polypeptide.

EXAMPLE VI

Epitope Tagging of Tir

The purpose of this EXAMPLE was to confirm that the 90 kDa tyrosine phosphorylated protein in epithelial membranes was the EPEC Tir protein. Two genetic fusions were constructed linking the sequence encoding either the T7 or HSV epitopes to the 5' or 3' of tir, respectively.

Figure 7A:
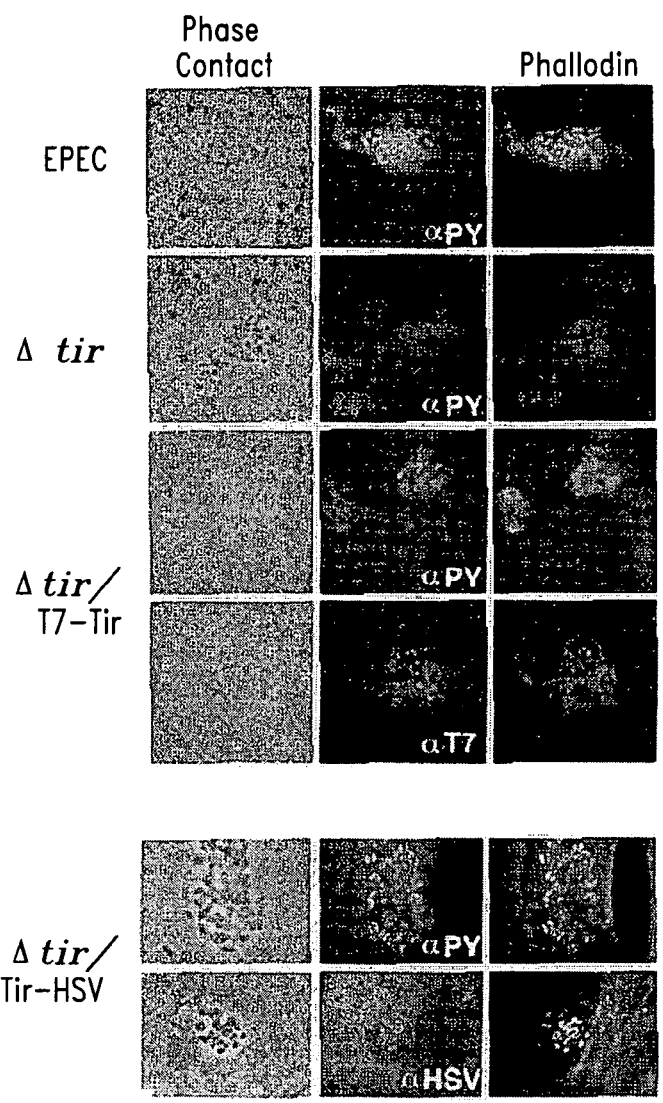
FIG. 7A shows that Tir mutant did not cause significant accumulation of phosphotyrosine proteins or actin beneath adherent bacteria. HeLa cells were infected for 3 hr. with EPEC, Δtir, or Δtir expressing a cloned T7-Tir or Tir-HSV fusion protein. Infected cells were fixed and labeled with either anti-PY, anti-T7, or anti-HSV antibodies followed by appropriate goat anti-mouse FITC conjugated antibodies. Polymerized actin was stained with phalloidin-Texas Red. Fluorescence microscopy of infected cells revealed typical pedestal formation with co-localization of both T7 and HSV epitopes and actin in characteristic horseshoe patterns.

Construction of T7-tir and tir-HSV fusions were performed as follows: Briefly, the tir gene was amplified by PCR introducing unique restriction sites to enable in frame fusions with the T7 or HSV sequences in the pET28a and pET27b set of vectors (Novagen). The tagged tir gene, lacking the His tag, was then cloned into a pACYC184 based vector for expression. The resulting plasmids were transformed into the EPEC tir allelic deletion strain and used to infect HeLa cells. Fluorescence microscopy of infected cells revealed typical pedestal formation with co-localization of both T7 and HSV epitopes and actin in characteristic horseshoe patterns (FIG. 7A). This phenotypic complementation with the tir-HSV construct, which encodes tir but not the downstream orfU gene, indicates that the phenotype of the tir deletion mutation is not due to a polar effect on the orfU gene product.

Figure 7B:
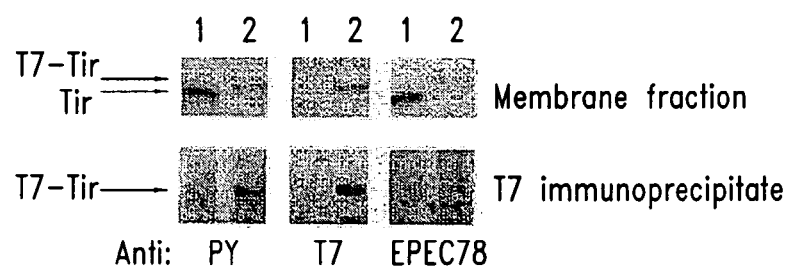
FIG. 7B shows that T7-Tir was detectable in HeLa cell membrane extracts using antibodies against EPEC 78 kDa, T7, and PY. To prove that T7-Tir was tyrosine phosphorylated, T7 specific antibodies were used to immunoprecipitate membrane fractions of HeLa cells infected with CVD206 or the T7-Tir strain. As expected the T7 antibodies did not immunoprecipitate the 90 kDa Tir protein, while they precipitated the slightly larger T7-Tir fusion protein which was recognized by antibodies against either PY, T7, or EPEC 78. HeLa cells were infected with the CVD206 (1) or Δtir expressing the T7-Tir fusion protein (2). The Triton soluble (membrane) fractions were then isolated and immunoprecipitated with anti-T7 antibodies. Membrane and T7 immunoprecipitates were loaded in triplicate and resolved by SDS-6% PAGE. After blotting to nitrocellulose the samples were then probed with anti-PY, anti-T7, or anti-EPEC 78 kDa antibodies. Solid arrows indicate the migrational position of Tir and shaded arrows that of T7-Tir. The addition of the T7 tag increased the apparent molecular mass of the Tir phosphorylated protein compared to that observed with CVD206. In contrast to T7-Tir, Tir itself did not cross-react with the T7 antibodies.

The membrane fractions of cells infected with EPEC expressing T7 tagged Tir were also compared to those infected with the intimin mutant CVD206. T7-Tir was detectable in HeLa cell membrane extracts using antibodies against EPEC 78 kDa, T7, and PY (FIG. 7B). The addition of the T7 tag increased the apparent molecular mass of the Tir phosphorylated protein compared to that observed with CVD206. In contrast to T7-Tir, Tir itself did not cross-react with the T7 antibodies (FIG. 7B).

T7 specific antibodies were used to immunoprecipitate membrane fractions of HeLa cells infected with CVD206 or the T7-Tir strain. As expected the T7 antibodies did not immunoprecipitate the 90 kDa Tir protein, while they precipitated the slightly larger T7-Tir fusion protein which was recognized by antibodies against either PY, T7, or EPEC 78 (FIG. 7B).

This proves that T7-Tir is tyrosine phosphorylated and of bacterial origin.

EXAMPLE VII

Intimin Binds to Tir from EPEC by Gel Overlay Experiments

The purpose of this EXAMPLE was to determine if intimin can bind directly to Tir secreted from EPEC.

Gel overlay experiments were performed using EPEC supernatants grown under conditions which express Tir. Gel overlays were performed as follows: Samples were resolved by 12% SDS-PAGE and transferred to nitrocellulose prior to blocking in 5% non-fat milk in Hyb75 (20 mM HEPES [pH 7.7]; 75 mM KCl; 0.1 mM EDTA; 2.5 mM $MgCl_2$; 1 mM DTT; 0.05% NP40) for 2 hr at room temperature. His-T7Intimin was incubated overnight in 1% BSA/TBS (Tris-buffered saline), washed and bound fusion detected by T7 antibodies (1:5000 in 1% BSA/TBS) followed by goat anti-mouse horseradish peroxidase (1:10,000 in 1% BSA/TBS plus 0.1% Tween®-20) using the ECL detection system (Amersham).

These supernatants were probed with purified His-T7Int fusion protein, which contains the 280 C-terminal residues of intimin. The fusion protein was constructed as follows: The MBP-Int genetic fusion was constructed, and MBP and MBP-Intimin fusions purified, as described elsewhere (Frankel et al., 1994). The same portion of intimin was cloned into pET28a to make a His-T7Int in frame fusion and purified using a agarose-nickel column as described by the supplier (Novagen).

Thus, EPEC growth culture supernatant was serially diluted, doped with a constant amount of uninfected HeLa membrane extract, resolved by SDS-PAGE and transferred to nitrocellulose before adding the His-T7Int peptide and detecting the bound fusion protein with anti-T7 antibodies. FIG. 7A shows that the His-T7Int protein specifically bound to a single 78 kDa band, subsequently identified as Tir by probing the same blot with anti-EPEC 78 kDa antibodies. This binding occurred in a concentration dependant manner. The level of Tir present in the supernatant, even at the highest concentration used, was below detection with Coomassie Blue.

The 280 C-terminal residues of intimin do not bind to $\beta_1$ integrins. Binding of MBP-Int to epithelial cells has been detected when the cells have been preinfected with EPEC, but not to uninfected cells or those infected with type III secretion or signaling mutants, cells which still express $\beta_1$ integrins. When MBP-Int is used to precipitate the 90 kDa form of Tir from epithelial membranes, $\beta_1$ integrins are not co-precipitated, despite their presence in the epithelial membrane extract used for precipitations. Additionally, using gel overlay systems, various intimin fusion proteins only bind to Tir but not to the larger molecular weight $\beta_1$ integrins (or any other epithelial membrane molecule) (FIG. 8A). Tir extracted from epithelial membranes was probed with polyclonal antibodies directed against $\beta_1$ integrins and have detected no crossreactivity. $\beta_1$ integrins are not co-localized beneath adherent EPEC on epithelial cells (although Tir is), and EPEC adheres strongly to the apical surface of polarized epithelial cells which do not contain known $\beta_1$ integrins. The reasons for these discrepancies remain unresolved, but the results strongly suggest that Tir is the main intimin receptor on cultured mammalian cells.

These data show that intimin does not bind to any HeLa cell membrane molecule; that under these conditions intimin can bind to unphosphorylated Tir; and that other EPEC secreted proteins are not needed to facilitate this binding.

EXAMPLE VIII

Intimin Binds to Tir from EPEC by ELISA

The purpose of this EXAMPLE was to develop an ELISA to examine the specificity of intimin interactions with EPEC secreted Tir.

ELISAs were carried out as previously described by Kenny et al., *Infection & Immunity* 65 (1997). For binding/competitive ELISAs, 100 µl of EPEC or tir supernatant grown under conditions that induce Tir secretion was added to Immulon 96-well (Dynatech Laboratories, Inc) plates. After blocking with 200 µl 0.1% Tween®-20/PBS, wells were incubated with a) 100 µl of His-T7Int (0.75 µg/ml in PBS) or 2-fold serial dilutions in PBS or b) 100 µl His-T7Int (0.75 µg/ml in PBS) containing 170 µg/ml MBP-Int or 85 µg/ml MBP in addition to 4-fold serial dilutions into PBS containing 0.75 µg/ml His-T7Int. Binding of the His-T7Int fusion was detected with T7 antibodies and visualized spectrophotometrically at absorbance wavelength A490 as previously described by Kenny et al., *Infection & Immunity* 65 (1997).

Figure 8B:
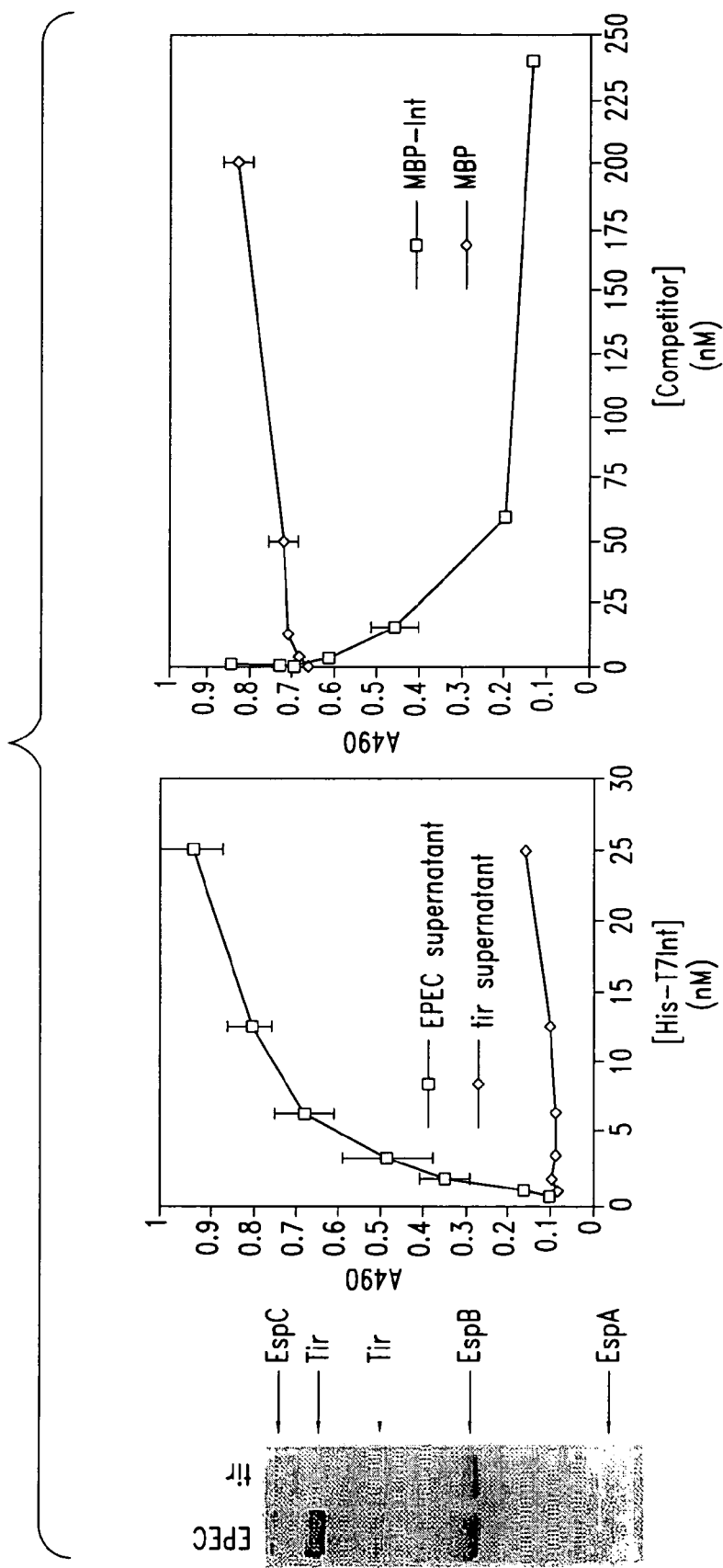
FIG. 8B shows that the presence of roughly equivalent levels of the other EPEC secreted proteins and the absence of Tir in the tir supernatant was confirmed by Coomassie staining and conventional ELISA probing supernatant dilutions with anti-EPEC 78 kDa or EspB antibodies. Serial dilutions of purified His-T7Int fusion protein was added to the coated ELISA plate and bound fusion protein detected using anti-T7 antibodies. Coomassie stained profile of secreted proteins derived from 1 ml of EPEC or tir supernatant used in binding assays (left panel). The middle panel demonstrates dose dependent binding of the His-T7Int fusion to Tir 100 µl EPEC or tir supernatant (in triplicate) was added to ELISA wells and incubated with serial dilutions of His-T7Int peptide. Binding of the His-T7Int protein was detected spectrophotometrically ($A_{490}$) using T7 specific antibodies as described in EXAMPLE VII. As shown in the middle panel, His-T7Int bound only to the wells containing Tir in the growth supernatant. This binding was in a dose dependent manner, with near saturation binding occurring at 75 ng/well (25 nM). The right panel demonstrates that binding of a constant amount of His-T7Int (75 ng/well) to EPEC supernatants containing Tir is competitively inhibited by increasing amounts of by MBP-Int, but not MBP. Results are shown±standard deviation. His-T7Int (75 ng/well) binding to immobilized EPEC supernatants was inhibited in a dose dependent manner by increasing concentrations of maltose binding protein (MBP)-intimin fusion peptide, but not by MBP alone. 50% inhibition of binding occurred with roughly equal molar amounts of both fusion proteins (25 nM). These results again emphasize that intimin can bind unphosphorylated Tir in a specific manner.

ELISA wells were coated with growth supernatant from EPEC or the isogenic tir mutant. The presence of roughly equivalent levels of the other EPEC secreted proteins and the absence of Tir in the tir supernatant was confirmed by Coomassie staining and conventional ELISA probing supernatant dilutions with anti-EPEC 78 kDa or EspB antibodies (FIG. 8B). Serial dilutions of purified His-T7Int fusion protein was added to the coated ELISA plate and bound fusion protein detected using anti-T7 antibodies. As shown in FIG. 8B (middle panel) His-T7Int bound only to the wells containing Tir in the growth supernatant. This binding was in a dose dependent manner, with near saturation binding occurring at 75 ng/well (25 nM). His-T7Int (75 ng/well) binding to immobilized EPEC supernatants was inhibited in a dose dependent manner by increasing concentrations of maltose binding protein (MBP)-intimin fusion peptide, but not by MBP alone (FIG. 8B, right panel). 50% inhibition of binding occurred with roughly equal molar amounts of both fusion proteins (25 nM).

These results again emphasize that intimin can bind unphosphorylated Tir in a specific manner.

EXAMPLE IX

Tir Isolated From EHEC

The purpose of this EXAMPLE was to investigate the structure of Tir in enterohemorrhagic *E. coli* (EHEC). The tir gene was cloned and its sequences were compared to those of enteropathogenic *E. coli* (EPEC). The amino acid sequence homology among the Tir polypeptides is shown in FIG. 9.

Cloning and sequence analysis of tir genes was done as follows: The DNA fragment encoding EHEC tir was obtained by PCR from EHEC chromosomal DNA using primers derived from the published sequence of enteropathogenic *E. coli*. Vent DNA polymerase was used for PCR to amplify chromosomal DNA from EHEC strains. The PCR reaction was carried out for thirty cycles of denaturation at 94° C. for one minute, annealing at 55° C. for one minute, and elongation at 72° C. for two minutes. The resulting product was ligated into the commercially available plasmid pBluescript and both strands were sequenced. DNA sequencing was done as follows: The DNA fragment encoding the tir genes was amplified by PCR using the primers, and EHEC chromosomal DNA as the DNA template. The resulting blunt end fragment was digested with SalI and cloned into the SalI-SmaI site of the commercially available plasmid pBluescript-II SK (+). The DNA sequence of EHEC tir was determined using the commercially available Taq DyeDeoxy™ kit. Open reading frames were found in the cloned regions and both of these DNA sequences were similar to EPEC tir.

These results show that EHEC encodes a tir gene, and that the predicted Tir polypeptide is highly conserved in EPEC and EHEC.

EXAMPLE X

Rabbit Model for EPEC Virulence

The purpose of this EXAMPLE was to show that EspA and EspB are critical for virulence. Using human volunteers, it has been shown that intimin is needed for full EPEC virulence (Donnenberg et al., *J. Clin. Inv.* 92: 1412–7 (1993)), and several animal models have documented the role of intimin in virulence. A natural rabbit EPEC infection model was used to demonstrate that EspA and EspB are critical for virulence.

RDEC-1 (SEQ ID NO:12), and its espA and espB mutant stains were inoculated by the orogastric route into young rabbits. Most RDEC-1 was found in die cecum and colon one week postinfection. However, the number of either mutant strain was greatly decreased in these tissues compared to the parent strain. RDEC-1 adhered specifically to the sacculus rotundas (follicle associated epithelium) and bacterial colonization was also observed in the cecum, indicating that the sacculus rotundas in the cecum is an important colonization site for this pathogen. The adherence levels of the ESpA⁻ and ESpB⁻ strains To the sacculus rotundas were 70 and 8000 times less than that of parent strain. These results show that the adherence ability and tissue tropism of RDEC-1 are dependent on the two Esp secreted proteins. Furthermore, EspB appears to play a more critical role than EspA in bacterial colonization and pathogenesis. This is the first demonstration that the enteropathogenic *E. coli* secreted proteins, EspA and EspB, which are involved in triggering of host cell signal transduction pathways, are also needed for colonization and virulence.

Animal infections were performed as follows: Overnight bacterial cultures were collected by centrifugation and resuspended in one ml of phosphate-buffered saline. New Zealand white rabbits (weight 1.0 to 1.6 kg) were fasted overnight, then five ml of 2.5% sterile sodium bicarbonate and one ml of RDEC-1 or espA or espB strains ($2.5 \times 10^{10}$) were inoculated into the stomach using orogastric tubes. The same dosage of bacteria was inoculated into each rabbit the following day.

Clinical assessments were performed as follows: Each rabbit was weighed daily and fecal shedding of bacteria were collected by rectal swabs and from stool pellets. Rectal swabs were rolled over one half of the surface of MacConkey plates containing nalidixic acid. Five stool pellets or same amount of liquid stool were collected from each rabbit and resuspended in three ml phosphate-buffered saline and 0.1 ml of each stool suspension was plated onto MacConkey plate containing nalidixic acid. The growth of nalidixic resistant colonies was scored as follows: O, no growth; 1, widely spaced colonies; 2, closely spaced colonies; 3, confluent growth of colonies.

Sampling and preparation of tissue were performed as follows: Tissues were excised immediately following sacrifice by intravenous injection of ketamine and overdosing with sodium phenobarbital.

The amount of bacterial colonization in intestinal tissues was assayed as follows: The intestinal segments (10 cm), except cecum, were doubly ligated at their proximal and distal ends, and dissected between the double ligated parts, then flushed with 10 ml of ice-cold phosphate-buffered saline. One gram of viscous contents from the cecum was added to 9 ml phosphate-buffered saline. The resulting phosphate-buffered saline suspensions were diluted and plated on MacConkey plates containing nalidixic acid.

The amount of bacterial adherence to intestinal tissues was assayed as follows: Tissue samples were excised using a 9 mm diameter cork punch, washed three times with phosphate-buffered saline, added to two ml of ice-cold phosphate-buffered saline, and homogenized with a homogenizer, then serial diluted samples were plated onto MacConkey plates. The numbers of bacteria adherent to each tissue per square centimeter were calculated as follows: $CFU/cm^2$=the bacterial number/plate×dilution factor×2 ml/~0.452

These data indicate that these molecules and the functions they perform are critical for pathogenesis. The intimate interactions that occur between EPEC secreted proteins and the host cell surface emphasize the complexity of host pathogen interactions, and provide valuable tools to exploit and study cellular function and bacterial disease, in addition to potential uses in therapeutics.

EXAMPLE XI

Development of a Bovine Vaccine Against EHEC

The purpose of this EXAMPLE is to provide a bovine vaccine enterohemorrhagic *E. coli*.

EHEC has been linked to many food-borne outbreaks and sporadic cases of hemorrhagic colitis and hemolytic uremic syndrome worldwide. One outbreak in 1993 on the west coast of the United States involved over 500 cases and the deaths of several young children. EHEC is the third most frequent cause of food-borne illness in the US. The most common epidemiologically-associated food is ground beef. EHEC causes no disease symptoms in cattle, but beef and dairy cattle carry EHEC in their intestinal tracts. Contamination of carcasses occurs during slaughter operations.

Cattle are vaccinated them with Tir, EspA, EspB, intimin, or combinations thereof. The adherence of EHEC to vaccinated cows is blocked by the bovine immune response. Vaccinated cattle therefore do not become EHEC carriers.

The use of vaccinated cattle reduces the occurrence of beef contaminated by enterohemorrhagic *E. coli*. The reduced release of contaminated foods into the marketplace consequently reducing, and perhaps even eliminating, the incidence of EHEC food-associated illnesses and their associated economic burdens.

EXAMPLE XII

Development of an Assay to Screen for Inhibitors of Tir Polypeptide Binding to Intimin The purpose of this EXAMPLE is to provide an assay to screen for a compound which interferes with the binding of a Tir polypeptide to intimin.

The binding of Tir polypeptide to intimin is measured under standard conditions. A Scatchard plot of the binding is generated to determine the binding affinity of Tir polypeptide to intimin.

Then, a candidate compound suspected of interfering with the binding of Tir polypeptide to intimin is added to a mixture or solution of Tir polypeptide and intimin. The binding of Tir polypeptide to intimin is then measured under the standard conditions. A Scatchard plot of the binding is generated to determine a change in the binding of Tir polypeptide to intimin.

The assay compares the binding of the Tir polypeptide to intimin in the presence of the compound to the binding of the Tir polypeptide in the absence of the compound. Compounds that interfere with the binding of Tir polypeptide to intimin are useful in the treatment of pathogens where the binding of Tir polypeptide to intimin is involved in pathogenesis, including such pathogens as EPEC and EHEC.

EXAMPLE XIII

A Method Differentiating Between EPEC and EHEC

The purpose of this EXAMPLE is to demonstrate a method for differentiating among pathogens that contain very similar virulence factors. An isolated strain of an attaching and effacing pathogen, either EPEC or EHEC, is used to infect tissue culture cells. The tissue culture cells are probed with anti-phosphotyrosine and anti-Tir antibodies. The binding of anti-phosphotyrosine and anti-Tir antibodies to the bacteria in the infected tissue culture cells is detected by both immunofluorescence or Western blots.

EPEC in the infected tissue culture cells show a positive response for both anti-phosphotyrosine and anti-Tir antibody binding. EHEC in the infected tissue culture cells show a positive response for anti-Tir antibody binding and a negative response for both anti-phosphotyrosine binding.

EXAMPLE XIV

Targeted Cell Delivery

The purpose of this EXAMPLE is to use the Tir-intimin system for targeted cell delivery HeLa cells in tissue culture are infected with an eaeA EPEC (intimin mutant) strain. A intimin containing delivery vehicle is constructed and introduced into the culture. The delivery vehicle is a liposome encapsulating β-galactosidase. After appropriate incubation, the cells are washed and stained with X-gal. A blue color indicates that β-galactosidase is delivered to the cell by the liposome. Control cells treated with non-intimin-containing liposome encapsulating β-galactosidase stain at detectably lower intensity.

The results of this EXAMPLE show that Tir is delivered to cells and that a vehicle which targets Tir can deliver biochemicals to these cells.

Although the invention has been described with reference to the presently preferred embodiments, it should be understood that various modifications can be made without departing from the spirit of the invention. Accordingly, the invention is limited only by the following claims.

What is claimed is:

1. An isolated polypeptide comprising the amino acid sequence as set forth in SEQ ID NO: 11.

2. An isolated Tir (translocated intimin receptor) polypeptide fragment comprising the amino acid sequence set forth in SEQ ID NO: 7.

3. An isolated Tir polypeptide fragment that consists of 8 consecutive amino acids of the amino acid sequence of SEQ ID NO: 11.

4. A fusion protein comprising an isolated Tir polypeptide that comprises the amino acid sequence of SEQ ID NO: 11, wherein the Tir polypeptide is fused to a non-Tir protein.

5. The fusion protein of claim 4 wherein the fusion protein comprise a cleavage site located between the Tir polypeptide and the non-Tir protein sequence.

6. The fusion protein of claim 4 wherein the non-Tir protein sequence is an immunoglobulin (Ig) Fc domain.

7. The fusion protein of claim 4 wherein the non-Tir protein is a marker polypeptide selected from the group consisting of an enzyme, a fluorescence protein, and a luminescent protein.

8. A pharmaceutical composition comprising the polypeptide of claim 1 or claim 3 in a pharmaceutically acceptable carrier.

* * * * *